United States Patent
Nakamura

(10) Patent No.: US 9,995,729 B2
(45) Date of Patent: Jun. 12, 2018

(54) MEASUREMENT DEVICE

(71) Applicant: KABUSHIKI KAISHA TOSHIBA, Minato-ku (JP)

(72) Inventor: Yoshiaki Nakamura, Yokohama (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 371 days.

(21) Appl. No.: 14/938,164

(22) Filed: Nov. 11, 2015

(65) Prior Publication Data

US 2016/0187294 A1    Jun. 30, 2016

(30) Foreign Application Priority Data

Dec. 26, 2014 (JP) ................................ 2014-264041

(51) Int. Cl.
*G01N 33/487* (2006.01)

(52) U.S. Cl.
CPC . *G01N 33/48721* (2013.01); *G01N 33/48728* (2013.01)

(58) Field of Classification Search
None
See application file for complete search history.

(56) References Cited

U.S. PATENT DOCUMENTS

| | | |
|---|---|---|
| 2013/0092541 A1 | 4/2013 | Drndic et al. |
| 2014/0158540 A1* | 6/2014 | Ohura ............. G01N 33/48721 204/543 |
| 2014/0202857 A1 | 7/2014 | Valbusa et al. |
| 2014/0374255 A1 | 12/2014 | Hongo et al. |

FOREIGN PATENT DOCUMENTS

| WO | WO 2013/136430 A1 | 9/2013 |
| WO | WO 2013/137209 A1 | 9/2013 |

OTHER PUBLICATIONS

Yasunori Kondo et al. "Validity of the Coulter Counter model ZBI as an international standard blood cell analyzer," Journal of Analytical Bio-Science, vol. 31, No. 5, Dec. 20, 2008, 8 pages. (with English Abstract).

* cited by examiner

*Primary Examiner* — Arun S Phasge
(74) *Attorney, Agent, or Firm* — Oblon, McClelland, Maier & Neustadt, L.L.P.

(57) ABSTRACT

According to one embodiment, a measurement device includes a first chamber, a second chamber, a partition provided between the first and second chambers, a through hole which is provided in the partition and with which the first chamber and the second chamber communicate each other, a first electrode provided in the first chamber, and a second electrode provided in the second chamber. The first electrode and the second electrode contain different metals or alloys at least in surface layers thereof, and a relationship of $Ia<Ib$ is satisfied, where $Ia$ is an ionization tendency of a metal or an alloy contained at least in the surface layer of the first electrode and $Ib$ is an ionization tendency of a metal or an alloy contained at least in the surface layer of the second electrode.

14 Claims, 12 Drawing Sheets

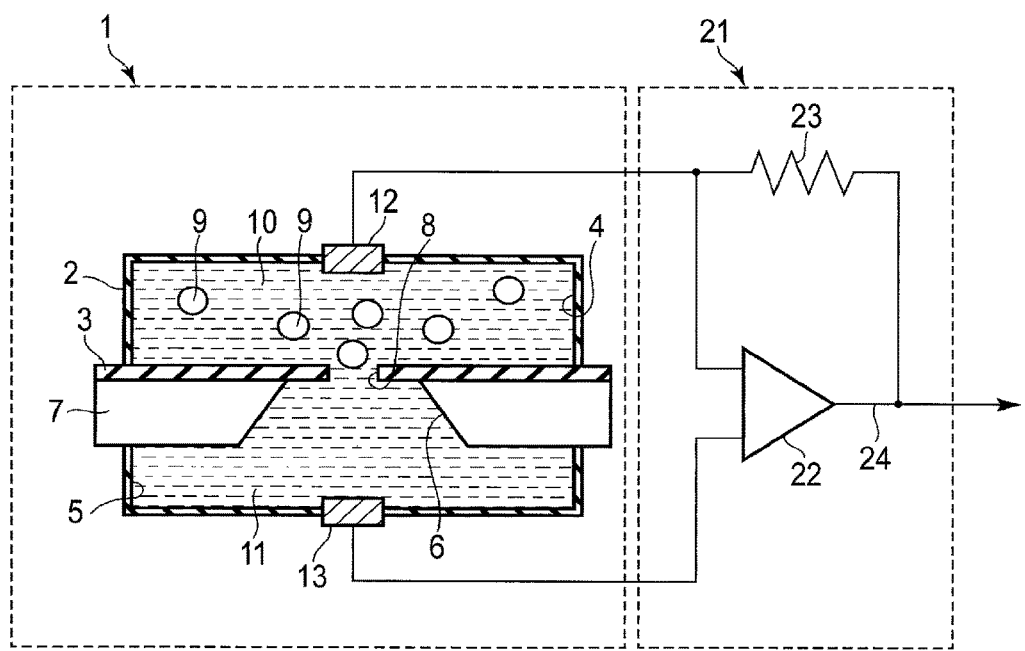
F I G. 1

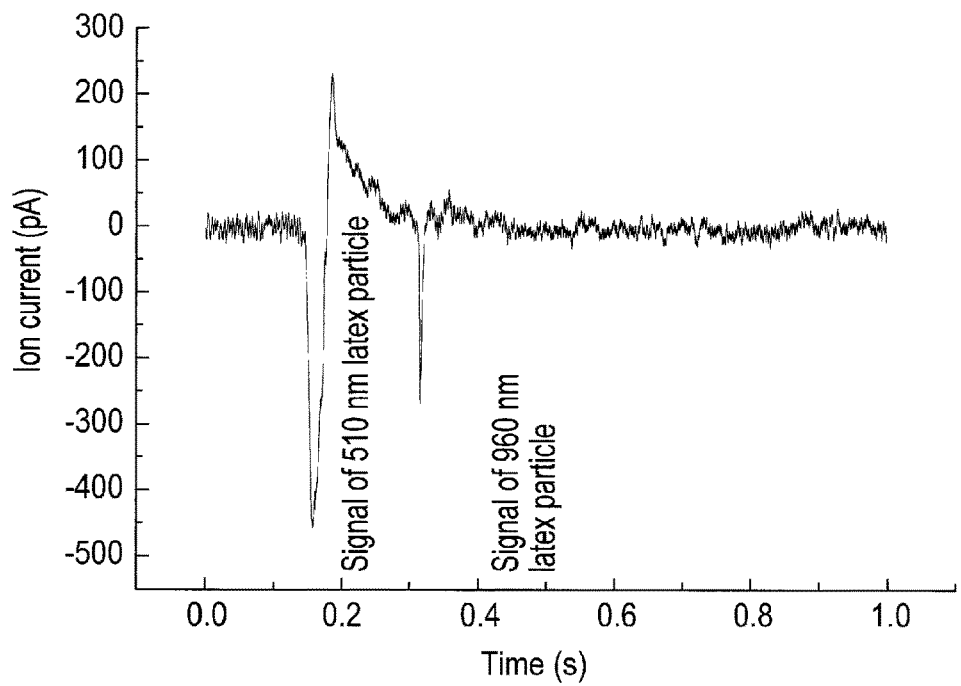
F I G. 4
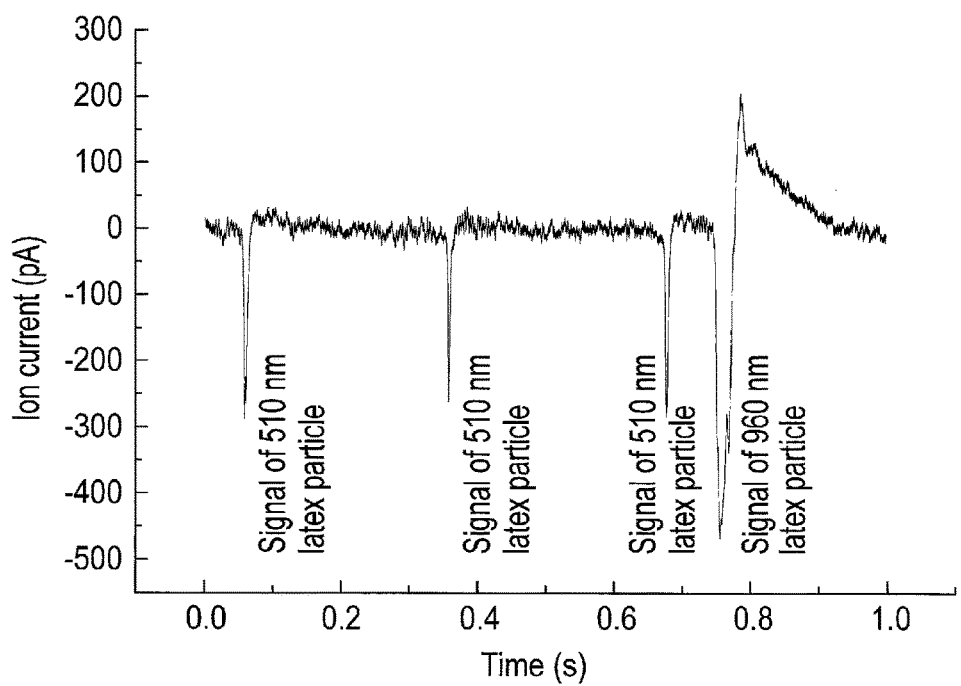
F I G. 5

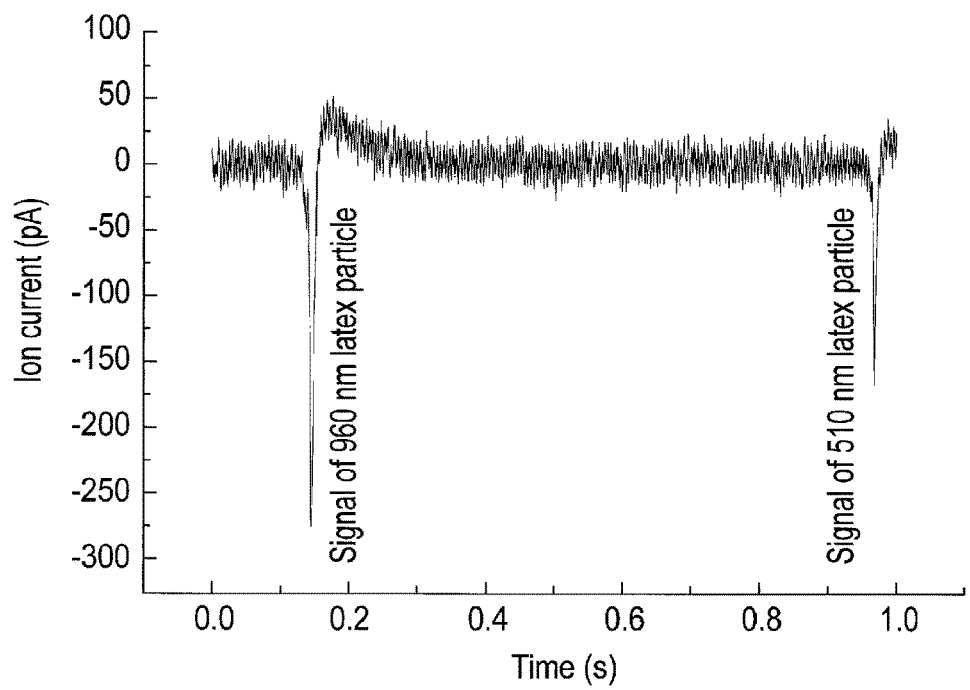
F I G. 10
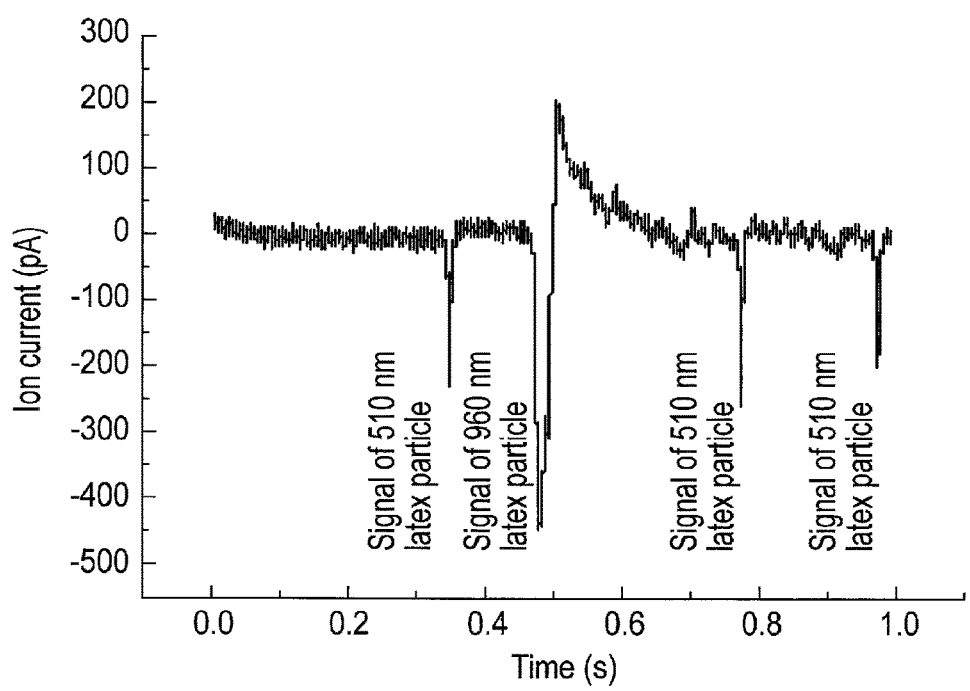
F I G. 11

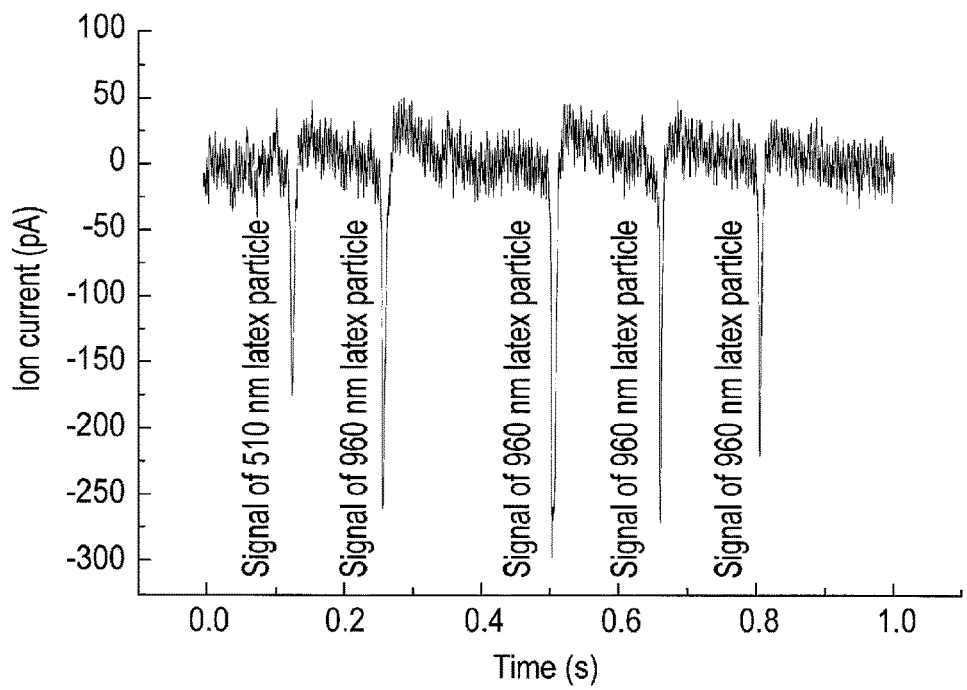
F I G. 12
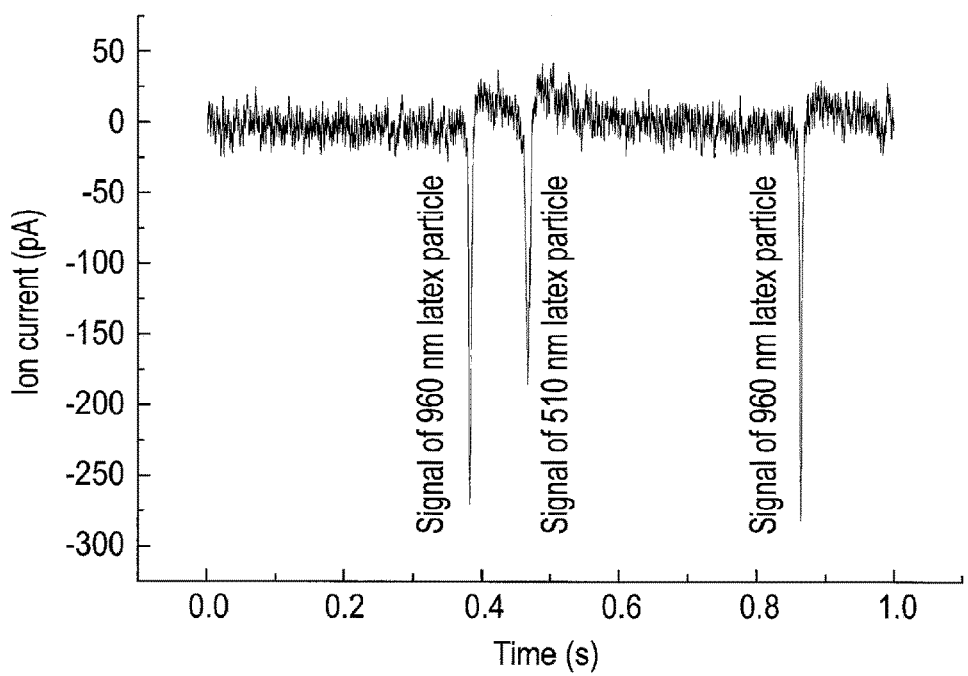
F I G. 13

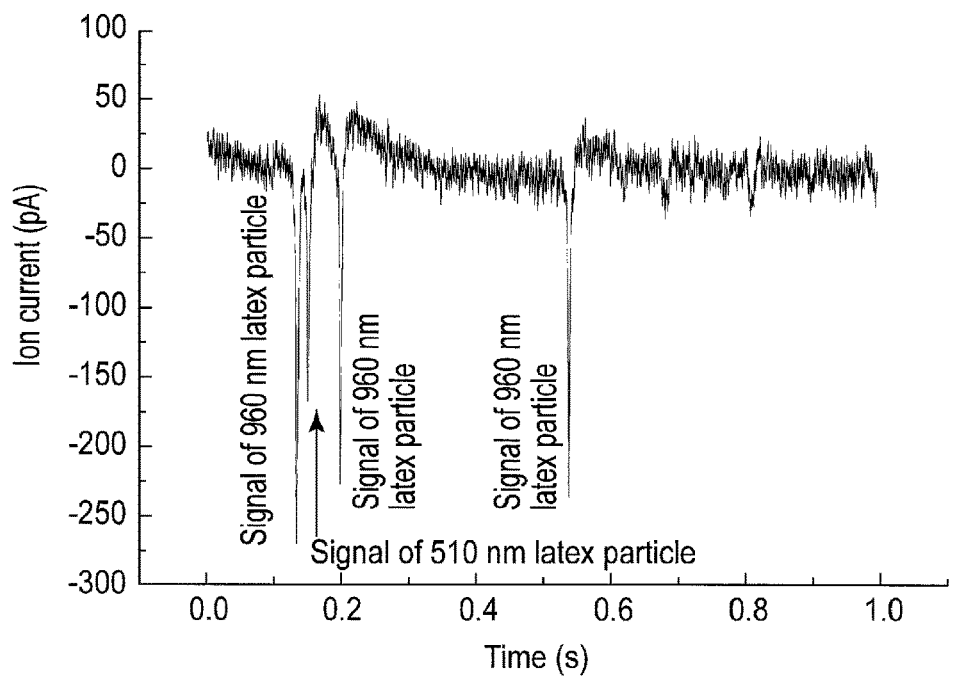
F I G. 14
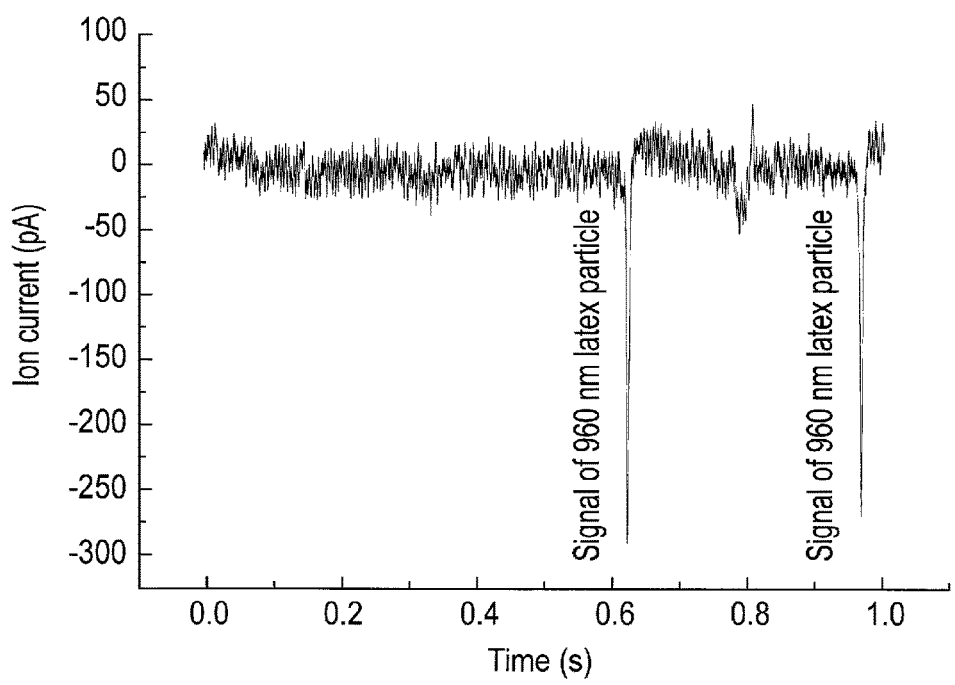
F I G. 15

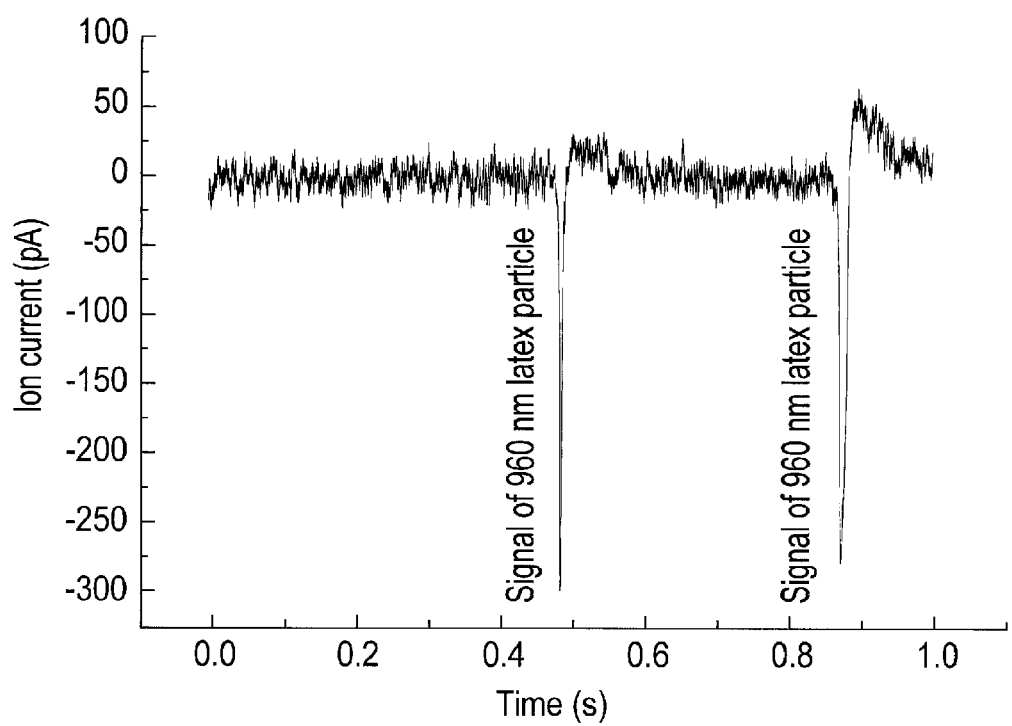
F I G. 22

MEASUREMENT DEVICE

CROSS-REFERENCE TO RELATED APPLICATIONS

This application is based upon and claims the benefit of priority from Japanese Patent Application No. 2014-264041, filed Dec. 26, 2014, the entire contents of which are incorporated herein by reference.

FIELD

Embodiments described herein relate generally to a measurement device configured to detect measurement target microparticles such as a bacterium, virus, protein, and DNA in a liquid phase.

BACKGROUND

With progress in the micromachining technique, a micro-nanopore-using analysis technique of a biopolymer such as a virus, protein, and DNA in a liquid phase has been developed.

There are two main micronanopore analysis techniques, as follows.

1) Detection Technique

Detecting a physical change (a change in current, for example) at the time when a target particle such as a virus, protein, and DNA passes through the pore; and 2) Transfer Control Technique Passing target particles such as a virus, protein, and DNA through in the pore having micrometer size or nanometer size by drawing the particles to the proximity of the pore.

A typical detection technique is performed as follows. A tank of a lid-opened structure is prepared and the tank is divided into a right chamber and a left chamber by an insulating plate. A pore is pierced through the insulating plate. The left chamber is filled with a first electrolytic solution and the right chamber is filled with a second electrolytic solution. For example, target particles are dispersed in the first electrolytic solution. First and second metal electrodes made of the same material are immersed in the first and second electrolytic solutions, respectively. The first and second metal electrodes are connected to a power source.

A measuring method of target particles using such a detection device will now be explained.

A desired voltage from the power source is applied between the first and second metal electrodes to supply a current through the first electrolytic solution, pore, and second electrolytic solution in this order. In this state, the target particles dispersed in the first electrolytic solution in the left chamber are transferred into the pore. When a particle enters the pore, resistivity between the first and second metal electrodes also changes based on the size of the particle. As a result, a value of the current through the first electrolytic solution, pore, and second electrolytic solution in this order changes. The size of the target particle can be detected by observing a time response-current change relationship.

Particles dispersed in the liquid phase are negatively charged (have a zeta potential) in general, and thus, a transfer control technique is adopted in many cases. The transfer control technique uses the voltage used in the detection technique to pass the target particles through the pore. That is, when a voltage is applied from the power source to the first and second electrodes, the potential of the first electrolytic solution with target particles dispersed therein is set to be negative and the potential of the second electrolytic solution is set to be positive. In this state, a repulsive force works on the negatively-charged target particles in the first electrolytic solution of negative potential, and the particles are electrically transferred to the second electrolytic solution through the pore.

Note that, if the power source of direct current is used, the flow of the current goes opposite to the transfer direction of the target particles.

If a high voltage is applied between the first and second electrolytic solutions to secure both the detection technique and the transfer control technique, the electrolytic solutions may be altered by electrolysis and the measurement may become unstable. Therefore, the applied voltage should be made as small as possible, specifically, approximately 1 to 2V. When the voltage of approximately 1 to 2V is applied, the current value changes depending on the property of the electrolytic solution and a physical size of the pore. Generally, a suitable current value during the voltage application should be set to an order of a nanoampere or a picoampere.

In other words, a device configured to measure a particle such as virus, protein, and DNA in a liquid phase using a pore is required to measure a current value of an order of a nanoampere or a picoampere at a response speed of approximately 100 to 500 KHz.

In such a device, a sensor including a pore and the like and a current measurement unit which measures the current running through the pore must be connected with the shortest distance to measure the current value of an order of a nanoampere or a picoampere at the response speed of approximately 100 to 500 KHz with a high signal-to-noise ratio.

However, conventionally, a power source must be connected in series to both the sensor including the pore and the like and the current measurement unit. If the power source is connected in series to the sensor and the current measurement unit, a length of the interconnection therebetween increases, and a stray capacitance of the interconnection itself increases. Furthermore, the power source itself may increase the stray capacitance. The increased stray capacitance causes a low response speed of a measured current value (because the capacitance components degrade the waveform sharpness) and a low signal-to-noise ratio of a measured current value.

Furthermore, if a commercial power source is used as the power source, the detection signal itself becomes minute, specifically, a microampere or a nanoampere. Therefore, alternating-current components of the commercial power source must be kept under a microampere or a nanoampere, or the alternating-current components overlapping the measurement result cause a great error. A complex power circuit structure is required to remove such alternating-current components of the commercial power source from the current value of an order of nanoampere or a picoampere, and such a complex power circuit structure will increase the stray capacitance and lower the response speed, and furthermore, manufacturing costs of the device will become high by such a complex structure.

BRIEF DESCRIPTION OF THE DRAWINGS

FIG. 1 is a schematic cross-sectional view which shows a measurement device of an embodiment.

FIG. 4 shows a time response-current change relationship obtained by the measurement device of example 3.

FIG. 5 shows a time response-current change relationship obtained by the measurement device of example 4.

FIG. 10 shows a time response-current change relationship obtained by the measurement device of example 9.

FIG. 11 shows a time response-current change relationship obtained by the measurement device of example 10.

FIG. 12 shows a time response-current change relationship obtained by the measurement device of example 11.

FIG. 13 shows a time response-current change relationship obtained by the measurement device of example 12.

FIG. 14 shows a time response-current change relationship obtained by the measurement device of example 13.

FIG. 15 shows a time response-current change relationship obtained by the measurement device of example 14.

FIG. 22 shows a time response-current change relationship obtained by the measurement device of example 21.

DETAILED DESCRIPTION

Figure 2:
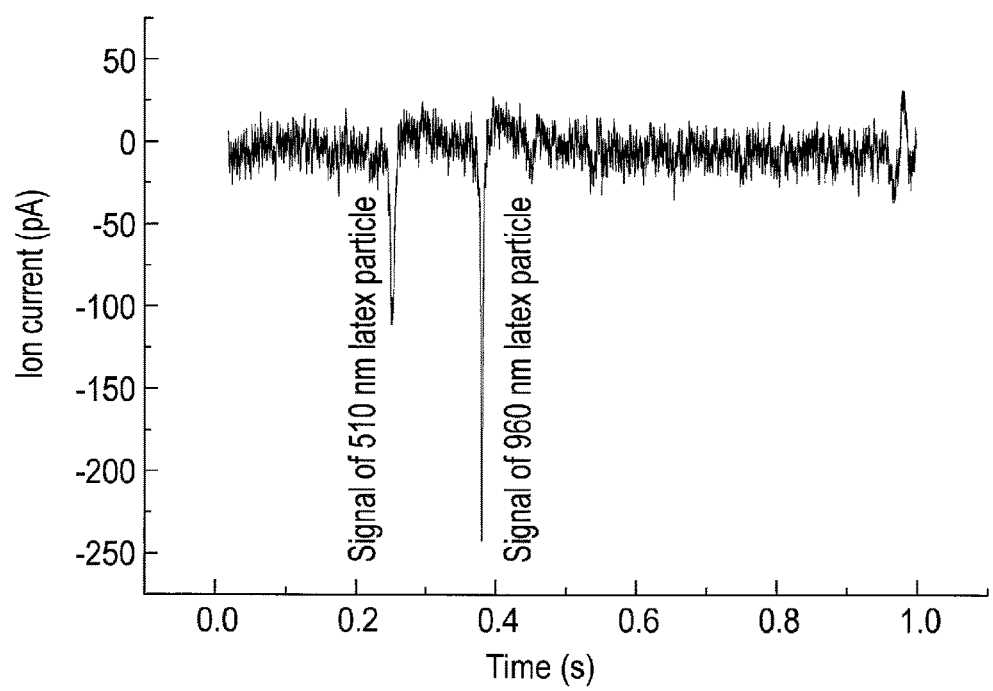
FIG. 2 shows a time response-current change relationship obtained by the measurement device of example 1.

In general, according to one embodiment, a measurement device includes a first chamber, a second chamber, a partition provided between the first chamber and the second chamber, a through hole which is provided in the partition and with which the first chamber and the second chamber communicate each other, a first electrode provided in the first chamber, and a second electrode provided in the second chamber. The first electrode and the second electrode contain different metals or alloys at least in surface layers thereof, and a relationship of Ia<Ib is satisfied. Where Ia is an ionization tendency of a metal or an alloy contained at least in the surface layer of the first electrode and Ib is an ionization tendency of a metal or an alloy contained at least in the surface layer of the second electrode.

Now, a measurement device of an embodiment will be described with reference to FIG. 1.

The measurement device of the embodiment includes a sensor 1 and a current measurement unit (current voltage converter circuit) 21.

The sensor 1 includes a measurement vessel 2. The measurement vessel 2 is divided by a partition 3 into the upper part and the lower part. The upper part of the measurement vessel 2 is a first chamber 4. The lower part of the measurement vessel 2 is a second chamber 5. A support plate 7 with a conical opening 6 pierced in its center is provided with the lower surface of the partition 3 for the support thereof. A through hole 8 is provided in the partition 3 overlapping the opening 6 of the support plate 7. The first and second chambers 4 and 5 communicate each other with the through hole 8. The through hole 8 is sufficiently small as compared to the opening 6. A first electrolytic solution 10 is filled in the first chamber 4, and a second electrolytic solution 11 without target particles dispersed therein is filled in the second chamber 5. A first electrode 12 shaped into, for example, a square pillar is provided in the upper wall of the container vessel 2 at the first chamber 4 to be partly or entirely immersed in the first electrolytic solution 10. A second electrode 13 shaped into, for example, a square pillar is provided in the lower wall of the measurement vessel 2 at the second chamber 5 to be partly immersed in the second electrolytic solution 11. The first and second electrodes 12 and 13 are, for example, provided with the walls of the container vessel 2 to be directly above and below the through hole 8 of the partition 3, respectively.

In the sensor 1 structured as above, the first and second electrodes 12 and 13 are made of different metals or alloys at least in the surface layers thereof. When target particles 9 are dispersed in the first electrolytic solution 10 in the first chamber 4, the ionization tendency of the metal or the alloy contained at least in the surface layer of the first electrode 12 is Ia, and the ionization tendency of the metal or the alloy contained at least in the surface layer of the second electrode 13 is Ib, wherein Ia<Ib. In one embodiment, the surface layer of the first electrode 12 is made of the ionization tendency Ia of the metal or the alloy and the surface layer of the second electrode 13 is made of the ionization tendency Ib of the metal or the alloy.

The above condition of Ia<Ib is determined based on the electrolytic solution in which target particles are dispersed for transference from one chamber to the other chamber through a through hole. An electrode having a smaller ionization tendency Ia is immersed in the electrolytic solution and an electrode having a larger ionization tendency Ib is immersed in an electrolytic solution with no target particles dispersed therein. That is, with the first and second electrodes 12 and 13 made of metals or alloys with an ionization tendency of Ia<Ib, a battery reaction (or a cell reaction) which will be explained later occurs, and a current from the second electrode 13 having a larger ionization tendency Ib flows in the second electrolytic solution 11, through hole 8, and first electrolytic solution 10 in this order, and reaches the first electrode 12 having a smaller ionization tendency Ia. Concurrently, the target particles 9 in the first electrolytic solution 10 with the first electrode 12 immersed therein are transferred through the through hole 8 to the second electrolytic solution 11 with the second electrode 13 immersed therein by the large-small relationship between the ionization tendencies. If such transference of the target particles is performed in the structure of FIG. 1 in which the first chamber 4 filled with the first electrolytic solution 10 with the target particles 9 dispersed therein is disposed in the upper part of the measurement vessel 2, the transference of the target particles 9 can be assisted by gravity.

A current voltage converter circuit 21 includes a current voltage converter amplifier 22 having input terminals to which the first and second electrodes 12 and 13 are connected, and a current voltage converter resistance 23 connected between an output terminal 24 and one of the input terminals of the current voltage converter amplifier 22. In the current voltage converter circuit 21, a weak current flowing between the first and second electrodes 12 and 13 is amplified by the current voltage converter amplifier 22, converted into voltage signals, and output from the output terminal 24 of the current voltage converter amplifier 22. The voltage signals are output to a voltage recording device which is not shown and recorded as a time response-current change relationship.

According to the measurement device of the embodiment, the first electrode 12 is at least partly immersed in the first electrolytic solution 10 in the first chamber 4, the second electrode 13 is immersed in the second electrolytic solution 11 in the second chamber 5, and the first and second electrolytic solutions 10 and 11 are continuous through the through hole 8 of the partition 3. In this sensor 1, the first and second electrodes 12 and 13 contain different metals or alloys at least in their surface layers, and satisfy the relationship of Ia<Ib to produce a battery reaction when the target particles 9 are dispersed in the first electrolytic solution 10 in the first chamber 4, wherein Ia is the ionization tendency of the metal or the alloy contained at least in the surface layer of the first electrode 12 and Ib is the ionization tendency of the metal or the alloy contained at least in the surface layer of the second electrode 13. By the battery reaction, a current runs from the second electrode 13 having a greater ionization tendency toward the first electrode 12 having a smaller ionization tendency flowing in the second electrolytic solution 11 in the second chamber 5, the through hole 8 of the partition 3, and the first electrolytic solution 10 with the target particles 9 dispersed therein in the first chamber 4 in this order. That is, the sensor 1 itself functions as a power source in the measurement device of the embodiment.

On the other hand, the target particles 9 which are negatively charged in general are dispersed in the first electrolytic solution 10 in the first chamber 4, and the target particles 9 are transferred from the first electrolytic solution 10 in the first chamber 4 with the first electrode 12 having a smaller ionization tendency immersed therein to the second electrolytic solution 11 in the second chamber 5 with the second electrode 13 having a larger ionization tendency immersed therein through the through hole 8 of the partition 3. That is, current runs from the second chamber 5 to the first chamber 4, and conversely, the target particles 9 are transferred from the first chamber 4 to the second chamber 5.

With the above relationship between the current flow and the transference of the target particles 9, a target particle 9 passing through the through hole 8 functions as a resistance with respect to the current flowing from the second electrode 13 to the first electrode 12 through the through hole 8. Before and after a target particle 9 passes through the through hole 8, a weak current running between the first and second electrodes 12 and 13 is amplified by the current voltage converter amplifier 22 of the current voltage converter circuit 21, and is converted into voltage signals to be output from the output terminal 24 to the voltage recording device which is not shown. The converted voltage signals are recorded as a time response-current change relationship. The recorded time response-current change relationship shows that a current (ion current) steeply drops from its regular reference value when a target particle 9 is passing through the through hole 8 of the partition 3, and then, the current returns to its reference value when the target particle 9 exits the through hole 8. When the target particle 9 is passing through the through hole 8 of the partition 3, the resistance increases in proportion to the size of the particle 9. Therefore, the size (particle size, for example) of each target particle 9 can be measured by calculating a degree of drop of the current from the reference value in a recorded time response-current change relationship.

The measurement vessel 2 is entirely or partly made of any publically-known material which is electrically and chemically inactive. The word partly means that only the inside part of the first chamber 4, the inside part of the second chamber 5, a part contacting the first electrode 12, and/or a part contacting the second electrode 13 may be made of such a material. For example, insulating ceramics such as glass, silica, alumina, and silicon nitride; general plastics such as polyethylene, and polypropylene; engineering plastics such as polyacetal, polycarbonate, polybutylene telephthalate; and rubbers such as elastomer are used for the measurement vessel.

The partition 3 is made of any publically-known material which is electrically and chemically inactive. For example, materials which can be used for the measurement vessel 2 include the above-mentioned insulating ceramics, plastics, and rubbers.

The shape of the through hole 8 provided in the partition 3 is determined based on the shape of target particles. The shape of the through hole 8 may be, for example, a circle, an oval, a combination of a circle and an oval, or a polygon such as a rectangle.

The diameter of the through hole 8 and the depth of through hole 8, which is corresponded to the thickness of the partition 3, are factors to be determined based on the intended measurement of target particles. This is because an error occurs when there are two or more target particles in the through hole at the same time during the measurement process. To avoid an error, the depth of the through hole is preferably as small as possible. That is, the depth of the through hole should be set to be at least the same as that of the target particle or less to secure the resolution in the measurement process. Additionally, the diameter of the through hole should be set to be greater than that of a target particle to prevent blockage of the through hole by the particle. If the measurement target is pollen, the diameter of the through hole should be at least 100 µm. If the measurement target is a bacterium, the diameter of the through hole should be at least 10 µm, and if the target is a virus, the diameter of the through hole should be at least 800 nm.

Considering a case where a measurement target is some kind of virus, a virus normally has a size of approximately 50 nm to 100 nm, and the depth of the through hole should be 50 to 100 nm for a size match, and the depth of the through hole should be reduced more to improve the resolution for better size measurement accuracy. As described later, a time response of the current value when a target particle exits the through hole must be measured accurately. To accurately grasp the shape of the target particle based on the time response of the current value, it should be measured with a response speed of 100 to 500 KHz in consideration of the depth of the through hole.

That is, the thickness of the partition 3 which is corresponded to the depth of the through hole 8 is required to be extremely small, in an order of tens to a few hundred nm. Therefore, the support plate 7 should be provided with the extremely thin partition 3 to support it from the downstream side of the transference direction of the target particles, as shown in FIG. 1. The support plate 7 may be made of silicon, for example.

The first chamber 4 and the second chamber 5 defined by the partition 3 may have the same volume or different volumes.

Note that first and second chambers of a measurement vessel defined by a partition may be prepared to be adjacent horizontally instead of a vertical arrangement as shown in FIG. 1. If such a horizontal arrangement is adopted, gravitation with respect to the target particle is the same in both right and left chambers. Therefore, the first chamber to contain an electrolytic solution with target particles dispersed therein can be arranged either in the right or left side of the measurement vessel.

The electrolytic solution filled in the first and second chambers may be, for example, a solution containing potassium chloride or sodium chloride, acetate buffer solution, phosphate buffer solution, citrate buffer solution, boric acid buffer solution, tartaric acid buffer solution, tris buffer solution such as tris/ethylenediaminetetraacetic acid (EDTA) solution, and phosphate buffer physiological saline.

The target particles 9 dispersed in the electrolytic solution 10 in the first chamber 4 may be, for example, pollen, a bacterium, a virus, a protein, and DNA.

Pollen is a spherical particle whose particle size is approximately 50 to 100 µm. Pollen is, for example, cypress pollen (approximately 30 to 45 µm), cedar pollen (approximately 30 to 40 µm), and pine pollen (approximately 45 to 55 µm).

The bacterium is, for example, anthrax bacillus, *Pasteurella pestis*, and *botulinus bacillus*. The anthrax bacillus generally has a breadth of approximately 1.0 to 1.2 µm and a particle size of approximately 5.0 to 2.0 µm. *Pasteurella pestis* generally has a breadth of approximately 1.5 to 2.0 µm and a particle size of approximately 1.5 to 2.0 µm. Botulinus bacillus generally has a breadth of approximately 0.5 to 2.0 µm and a particle size of approximately 2.0 to 10 µm.

The virus is, for example, a smallpox virus, bird flu virus, SARS virus, foot and mouth disease virus, and Ebola virus. The smallpox virus generally has a particle size of approximately 200 nm. The bird flu virus generally has a particle size of approximately 80 to 130 nm. The SARS virus generally has a particle size of approximately 60 to 220 nm. The foot and mouth disease virus generally has a particle size of approximately 21 to 25 nm. The ebola virus is a string-like virus having a size of approximately 80 to 800 nm.

Shapes of the first and second electrodes 12 and 13 are square pillars, or any polygonal pillars other than square pillars, cylinders, or needles. The first and second electrodes 12 and 13 may be positioned at any part of the wall of the measurement vessel 2 of the first chamber 4 side at which the first electrolytic solution is filled with the measurement particles dispersed therein and the wall of the measurement vessel 2 of the second chamber 5 side at which the second electrolytic solution is filled, respectively.

As mentioned above, the first and second electrodes 12 and 13 contain different metals or alloys at least in their surface layers, and Ia<Ib is satisfied. Wherein the ionization tendency of the metal or alloy contained at least in the surface layer of the first electrode 12 is Ia, and the ionization tendency of the metal or alloy contained at least in the surface layer of the second electrode 13 is Ib. When the relationship Ia<Ib is satisfied, the battery reaction will occur as described above. The current of the electromotive force in this battery reaction should be kept under 200 nA. For example, a bias voltage is applied to the voltage generated in the battery reaction to keep the current under 200 nA. If a current over 200 nA runs through the through hole 8 of the partition 3, the partition 3 in the proximity of the through hole 8 may be electrolyzed and an error may occur in a measurement result.

Exemplary metal materials have the following large-small relationship of ionization tendency. Mg>Be>Al>Ti>Zr>Mn>Ta>Zn>Cr>Fe>Cd>Co>Ni>Sn>Pb>Cu>Ag>Pd>Pt>Au.

Exemplary combinations of metals and alloys used for the surface layers of the first and second electrodes satisfying the relationship of Ia<Ib are as follows.

(1) Second electrode: Ag/AgCl (greater ionization tendency), and first electrode: at least one metal selected from a group consisting of Al, Cu, W, Ti, Ni, and Co or an alloy of the aforementioned metals.

(2) Second electrode: Al (greater ionization tendency), and first electrode: at least one metal selected from a group consisting of Au, Pt, Cu, Ti, Ni, Co, and Ti or an alloy of the aforementioned metals.

(3) Second electrode: Cu (greater ionization tendency), and first electrode: at least one metal selected from a group consisting of Au, Pt, and Ag or an alloy of the aforementioned metals.

(4) Second electrode: Ni (greater ionization tendency), and first electrode: at least one metal selected from a group consisting of Au, Pt, Ag, and Cu or an alloy of the aforementioned metals.

(5) Second electrode: Co (greater ionization tendency), and first electrode: at least one metal selected from a group consisting of Pt, Ni, Cu, and Au or an alloy of the aforementioned metals.

(6) Second electrode: W (greater ionization tendency), and first electrode: at least one metal selected from a group consisting of Au, Pt, Ag, Cu, Ni and Co or an alloy of the aforementioned metals.

(7) Second electrode: Ti (greater ionization tendency), and first electrode: at least one metal selected from a group consisting of Au, Pt, Ag, Cu, and Ni or an alloy of the aforementioned metals.

(8) Second electrode: Al alloy (greater ionization tendency), and first electrode: at least one metal selected from a group consisting of Au, Pt, Cu, Ni, Co, and Ti or an alloy of the aforementioned metals.

(9) Second electrode: Ni alloy (greater ionization tendency), and first electrode: at least one metal selected from a group consisting of Au, Pt, Ag, and Cu or an alloy of the aforementioned metals.

(10) Second electrode: Al (greater ionization tendency), and first electrode: an Ni alloy, Cu alloy, or W alloy.

(11) Second electrode: Cu (greater ionization tendency), and first electrode: an Ag alloy.

AgCl used for the second electrode is ranked greater than Al in the above ionization tendency relationship.

The alloy (made of two metals, for example) used for the first electrode of smaller ionization tendency may be composed such that a metal having smaller ionization tendency occupies 50 weight % or more of the alloy, and may be composed such that the metal occupies 80 weight % or more of the alloy, or more preferably 90 weight % or more of the alloy in consideration of higher durability of the electrode.

The alloy (made of two metals, for example) used for the second electrode of greater ionization tendency may be composed such that a metal having greater ionization tendency occupies 50 weight % or more of the alloy, and may be composed such that the metal occupies 80 weight % or more of the alloy, or more preferably 90 weight % of more of the alloy in consideration of higher durability of the electrode.

Combinations of metals or alloys used for the surface layers of the first and second electrodes to satisfy the relationship of Ia<Ib should be determined such that a potential difference between the first and second electrodes produces an electromotive force of 0.05 V or more.

Specifically, a combination of metals or alloys used for the surface layers of the first and second electrodes to satisfy the relationship of Ia<Ib should be determined as follows, for example, to achieve a potential difference between the first and second electrodes to produce an electromotive force of approximately 0.05 V or more and a linearity of good voltage-current characteristics. (1) First electrode: Al, and second electrode: Ag/AgCl (AgCl made as a coating of Ag). (2) First electrode: Au, and second electrode: Al. (3) First electrode: Pt, and second electrode: Al. (4) First electrode: Cu, and second electrode: Al. (5) First electrode: Ti, and second electrode: Al. (6) First electrode: Au, and second electrode: Cu. (7) First electrode: Pt, and second electrode: Cu. (8) First electrode: Ag, and second electrode: Cu. (9) First electrode: Au, and second electrode: Ni. (10) First electrode: Pt, and second electrode: Ni. (11) First electrode: Ag, and second electrode: Ni. (12) First electrode: Au, and second electrode: Co. (13) First electrode: Au, and second electrode: W. (14) First electrode: Pt, and second electrode: W. (15) First electrode: Cu, and second electrode: W. (16) First electrode: Au, and second electrode: Ti. (17) First electrode: Pt, and second electrode: Ti. (18) First electrode: Cu, and second electrode: Ti.

Note that the surfaces of the first and second electrodes can be coated by natural oxidization.

The first and second electrodes containing different metals or alloys at least in their surface layers may be made based on the following principles.

(1) First electrode is made of a metal or an alloy, and second electrode is made of a metal or an alloy which is different from that of first electrode.

(2) First electrode is made of a metal or an alloy, and second electrode is composed of a second electrode main body and a second surface layer provided on the surface of the second electrode main body, the second surface layer being made of a metal or an alloy which is different from that of the first electrode.

(3) First electrode is composed of a first electrode main body and a first surface layer provided on the surface of the first electrode main body, the first surface layer being made of a metal or an alloy, and second electrode is made of a metal or an alloy which is different from that of the first surface layer of the first electrode.

(4) First electrode is composed of a first electrode main body and a first surface layer provided on the surface of the first electrode main body, the first surface layer being made of a metal or an alloy, and second electrode is composed of a second electrode main body and a second surface layer provided on the surface of the second electrode main body, the second surface layer being made of a metal or an alloy which is different from that of the first surface layer of first electrode.

In an electrode composed of an electrode main body and a surface layer provided on the surface of the electrode main body, the ionization tendency changes depending on a metal or an alloy used in the surface layer. Thus, the electrode main body can be made of a metal or an alloy which is different from the surface layer. Specifically, in consideration of the above large-small relationship of ionization tendency, the first electrode can be made of a material of smaller ionization tendency such as Au, Pt, and Pd and the second electrode can be made of a material of relatively high ionization tendency such as Co, and Ni. The former materials are expensive and the latter materials are rare. If the electrode is composed of an electrode main body and a surface layer, the electrode main body can be made of a cheap metal such as iron or iron alloy while the surface layer is made of the above expensive or rare materials. Therefore, the manufacturing costs can be reduced as compared to a case where the electrodes are made of a single metal such as Au.

The surface layer is provided at least on the surface of the electrode main body which is contacted with the electrolytic solution in the chamber.

The formation of the surface layer may be performed through, for example, plating, vacuum deposition, chemical vapor deposition, and sputtering deposition. A thickness of the surface layer should be approximately 1 to 10 μm. Specifically, the surface of the second electrode having greater ionization tendency gradually dissolves in the electrolytic solution during the battery reaction, and the surface layer of the second electrode should be relatively thick such as 1 to 100 μm.

The measurement device of the above embodiment comprises a first chamber to be filled with a first electrolytic solution in which target particles are dispersed and a second chamber to be filled with a second electrolytic solution, the first and second chambers communicate with each other with a through hole in a partition, and the device comprises first and second electrodes provided with walls of a measurement vessel corresponding to the first and second chambers to be immersed in the first and second electrolytic solutions, respectively, wherein the at least surface layers of the first and second electrodes are made of metals or alloys exerting ionization tendencies of a certain large-small relationship, and a sensor itself functions as a power source caused by battery reaction. Consequently, the sensor can be connected to a current measurement unit with the shortest distance and stray capacitance caused by redundant connection can be reduced. A change in current running time in a microampere or a nanoampere order can be measured when a target particle exits the through hole of the sensor with faster response speed and higher signal-to-noise ratio as compared to a conventional measurement device. Therefore, accuracy of the measurement of size of microparticles such as a virus, protein, and DNA can be improved and the devise structure can be simplified.

EXAMPLES

Hereinafter, examples will be explained with reference to the measurement device of FIG. 1.

Example 1

Sensor 1 includes a glass measurement vessel 2. A glass partition 3 (10 mm long×10 mm wide×0.5 mm thickness) defines the upper part and the lower part of the measurement vessel 2 such that a first chamber 4 is prepared above the partition 3 in the measurement vessel 2 and a second chamber 5 is prepared below the partition 3 in the measurement vessel 2. A silicon support plate 7 is provided with the lower surface of the partition 3 with a conical-shaped opening 6 (having a top diameter of φ 0.004 mm and a base diameter of 0.46 mm) pierced through the center part for support of the partition 3. A micro through hole 8 is provided the partition 3 to correspond to the opening 6 of the support plate 7 such that the first and second chambers 4 and 5 communicate with each other and the through hole 8 has a 2 μm diameter which is sufficiently small as compared to the opening 6. A first electrolytic solution 10 is a tris/ethylene-diaminetetraacetic acid (EDTA) buffer solution (TE buffer solution) with target particles 9 dispersed therein at room temperature, and is filled in the first chamber 4. A second electrolytic solution 11 is the same TE buffer solution without the particles 9 and is filled in the second chamber 5. The TE buffer solution is a mixture of 1 M Tris-HCl buffer solution of 5 mL and 0.5M EDTA buffer solution of 1 mL diluted with pure water to 500 mL.

A square pillar-shaped first electrode 12 is made of an aluminum metal (a product of Nilaco, purity of 99.99%) and is provided in the upper wall of the measurement vessel 2 at the first chamber 4 to be at least half immersed in the height direction in the first electrolytic solution 10. A square pillar-shaped second electrode 13 is made of Ag/AgCl and is provided in the lower wall of the measurement vessel 2 at the second chamber 5 to be at least half immersed in the height direction in the second electrolytic solution 11. Note that Ag/AgCl of the second electrode 13 is square pillar-shaped silver (produced by Nilaco, purity of 99.99%) subjected to five minute constant current electrolysis in a KCl solution of concentration of 0.1 mol in a condition of 0.3 mA/cm$^2$ and to a silver-chloride treatment of the surface of the square pillar-shaped silver. That is, metal materials are determined such that the ionization tendency of the second electrode 13 becomes greater than that of the first electrode 12.

A current voltage converter circuit 21 includes a current voltage converter amplifier (trans impedance amplifier) 22 having input terminals connected to the first and second electrodes 12 and 13 and a current voltage converter resistance 23 connected between an output terminal 24 of the current voltage converter amplifier 22 and one of the input terminals. In the current voltage converter circuit 21, a weak current running between the first and second electrodes 12 and 13 is amplified by the current voltage converter amplifier 22 and converted to voltage signals. The converted voltage signals are output from the output terminal 24 of the current voltage converter amplifier 22. The current voltage converter circuit 21 is designed to have the sensitivity to convert a current value of 1 nA to a voltage of 1 V and a response speed of 250 KHz.

Note that the input terminals connecting the first and second electrodes 12 and 13 to the current voltage converter amplifier 22 are prepared with the shortest distance to reduce an influence of external noise in the current measurement process as much as possible.

Initially, the first and second electrolytic solutions 10 and 11 (TE buffer solution at room temperature) were filled in the first and second chambers 4 and 5, respectively, and a voltage between the first electrode 12 and the second electrode 13 was measured by a multimeter (made by Hewlett Packard). A measured potential difference between the first and second electrodes 12 and 13 caused by the aforementioned battery reaction was approximately 0.702 V.

Then, target particles 9 were dispersed in the first electrolytic solution 10 (TE buffer solution) in the first chamber 4. The target particles 9 were a mixture of polystyrene latex particles having a 510 nm diameter and polystyrene latex particles having a 960 nm diameter, and were added in the first electrolytic solution 10 such that the polystyrene latex particles having a 510 nm diameter were dispersed in a concentration of $5 \times 10^7$ particles/mL and the polystyrene latex particles having a 960 nm diameter were dispersed in a concentration of $1 \times 10^7$ particles/mL.

The target particles 9 prepared as above were dispersed in the first electrolytic solution 10, and in this state, a potential difference of approximately 0.702 V was produced from the second electrode 13 to the first electrode 12 through the through hole 8 of the partition 3, and the potential difference produced a base current of approximately 70 nA running therebtween. The target particles 9 moved from the first electrolytic solution 10 in the first chamber 4 with the first electrode 12 immersed therein to the second electrolytic solution 11 in the second chamber 5 with the second electrode 13 immersed therein through the through hole 8 of the partition 3. Empirically, if a base current is 200 nA or more, a buffer solution itself tends to be electrolyzed and a metal electrode tends to be electrolyzed at a part contacting the solution, physical properties of the buffer solution changes by the electrolysis of the buffer solution, and a base current value changes with the elapse of time. That is, such a base current as 200 nA or more causes lower measurement accuracy and shortened electrode life, and thus, a base current should be reduced as much as possible. The weak current running between the first and second electrodes 12 and 13 was treated by the current voltage converter circuit 21 and was recorded by a voltage recording device which is not shown. As a result, a time response-current change relationship indicative of a change in current (ion current) with respect to a recorded time (1.0 seconds) was measured as in FIG. 2. In FIG. 2, the base current value having a characteristic value was shifted to 0 pA as an absolute value of the current.

As is evident from FIG. 2, a base line of noise of the current progresses within an amplitude of approximately 40 pA (P-P). When a latex particle of 510 nm diameter passes through the through hole of 2 um diameter, a drop of approximately 100 pA in the current value was observed, and when a latex particle of 960 nm diameter passes through the through hole, a drop of approximately 250 pA in the current value was observed. Therefore, a drop ratio (degree of drop) of the current value measured when a smaller 510 nm latex particle passes through the through hole is less than that of the current value measured when a larger 960 nm latex particle passes through the through hole, and as is evident from this point, there is a correlation between the size of the latex particle and the degree of drop of current value.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared in advance. The time response-current change relationship shown in FIG. 2 is compared to the reference data, and the particle size of each latex particle (target particle) can be acquired.

Example 2

A measurement device having the structure shown in FIG. 1 was prepared as in example 1 except that a first electrode 12 is made of Au and a second electrode 13 is made of Al which has greater ionization tendency as compared to Au of the first electrode 12.

Initially, electrolytic solutions 10 and 11 (phosphate buffer solution at room temperature) were filled in the first and second chambers 4 and 5, and in this state, a voltage between the first electrode 12 and the second electrode 13 was measured as in example 1. As a result, a potential difference between the first and second electrodes 12 and 13 was approximately 0.611 V. Note that the phosphate buffer solution used was a 10×PBS buffer (pH 7.4), which is a genetic engineering research product of Wako Pure Chemical Industries, Ltd., Code No. 314-90185, diluted ten-fold with pure water.

Figure 3:
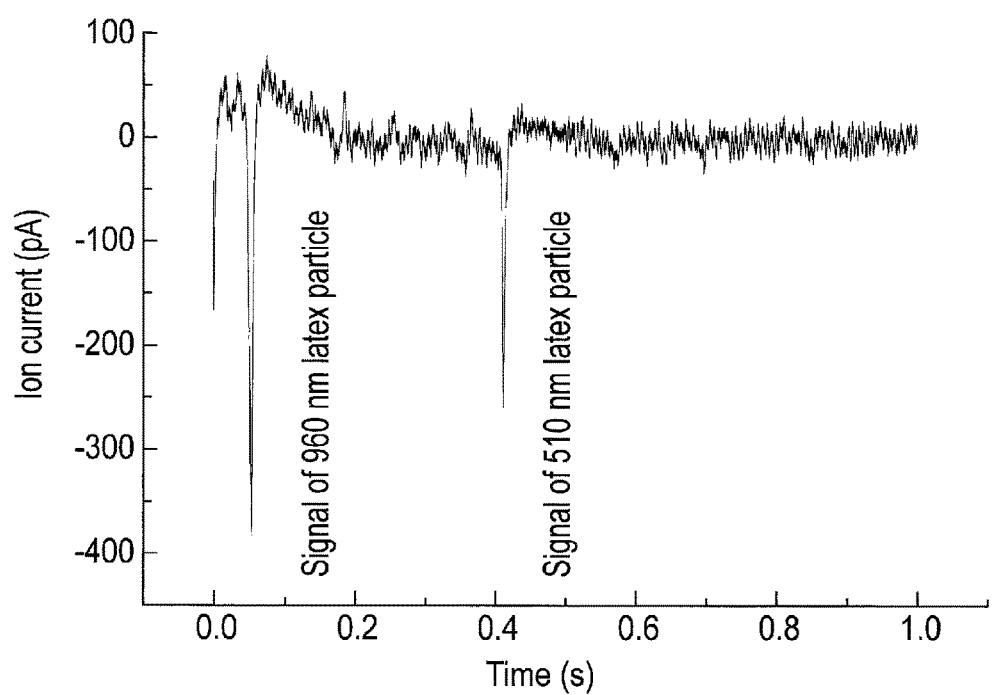
FIG. 3 shows a time response-current change relationship obtained by the measurement device of example 2.

Then, target particles 9 were dispersed in the first electrolytic solution 10 (phosphate buffer solution) in the first chamber 4. The target particles 9 were a mixture of polystyrene latex particles having a 510 nm diameter and polystyrene latex particles having a 960 nm diameter, and were dispersed in the solution 10 in the same concentration as in example 1. Then, the treatment as in example 1 was performed and a time response-current change relationship indicative of a change in current (ion current) with respect to a recorded time (1.0 seconds) was measured as in FIG. 3. In FIG. 3, the base current value having a characteristic value was shifted to 0 pA as an absolute value of the current.

As is evident from FIG. 3, a base line of noise of the current progresses within an amplitude of approximately 40 pA (P-P). When a latex particle of 510 nm diameter passes through the through hole of 2 μm diameter, a drop of approximately 250 pA in the current value was observed, and when a latex particle of 960 nm diameter passes through the through hole, a drop of approximately 390 pA in the current value was observed. Therefore, as explained in the section of example 1, there is evidently a correlation between the size of latex particle and the degree of drop of current value.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 3 is compared to the reference data, and the particle size of each latex particle (target particle) can be acquired.

Example 3

A measurement device having the structure shown in FIG. 1 was prepared as in example 1 except that a first electrode 12 is made of Pt and a second electrode 13 is made of Al which has a greater ionization tendency as compared to Pt of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.884 V.

Then, target particles 9 were dispersed in the first electrolytic solution 10 (phosphate buffer solution) in the first chamber 4. The target particles 9 were a mixture of polystyrene latex particles having a 510 nm diameter and polystyrene latex particles having a 960 nm diameter, and were dispersed in the solution 10 in the same concentration as in example 1. Then, the treatment as in example 1 was performed and a time response-current change relationship indicative of a change in current (ion current) with respect to a recorded time (1.0 seconds) was measured as in FIG. 4. In FIG. 4, the base current value having a characteristic value was shifted to 0 pA as an absolute value of the current.

As is evident from FIG. 4, a base line of noise of the current progresses within an amplitude of approximately 50 pA (P-P). When a latex particle of 510 nm diameter passes through the through hole of 2 μm diameter, a drop of approximately 250 pA in the current value was observed, and when a latex particle of 960 nm diameter passes through the through hole, a drop of approximately 450 pA in the current value was observed. Therefore, as explained in the section of example 1, there is evidently a correlation between the size of latex particle and the degree of drop of current value.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 4 is compared to the reference data, and the particle size of each latex particle (target particle) can be acquired.

Example 4

A measurement device having the structure shown in FIG. 1 was prepared as in example 1 except that a first electrode 12 is made of Cu and a second electrode 13 is made of Al which has a greater ionization tendency as compared to Cu of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.74 V.

Then, target particles 9 were dispersed in the first electrolytic solution 10 (phosphate buffer solution) in the first chamber 4. The target particles 9 were a mixture of polystyrene latex particles having a 510 nm diameter and polystyrene latex particles having a 960 nm diameter, and were dispersed in the solution 10 in the same concentration as in example 1. Then, the treatment as in example 1 was performed and a time response-current change relationship indicative of a change in current (ion current) with respect to a recorded time (1.0 seconds) was measured as in FIG. 5. In FIG. 5, the base current value having a characteristic value was shifted to 0 pA as an absolute value of the current.

As is evident from FIG. 5, a base line of noise of the current progresses within an amplitude of approximately 40 pA (P-P). When a latex particle of 510 nm diameter passes through the through hole of 2 μm diameter, three drops of approximately 280, 255, and 280 pA in the current value were observed within 1.0 seconds, and when a latex particle of 960 nm diameter passes through the through hole, a drop of approximately 450 pA in the current value was observed. Therefore, as explained in the section of example 1, there is evidently a correlation between the size of latex particle and the degree of drop of current value.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 5 is compared to the reference data, and the particle size of each latex particle (target particle) can be acquired.

Example 5

A measurement device having the structure shown in FIG. 1 was prepared as in example 1 except that a first electrode 12 is made of Ti and a second electrode 13 is made of Al which has a greater ionization tendency as compared to Ti of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.72 V.

Figure 6:
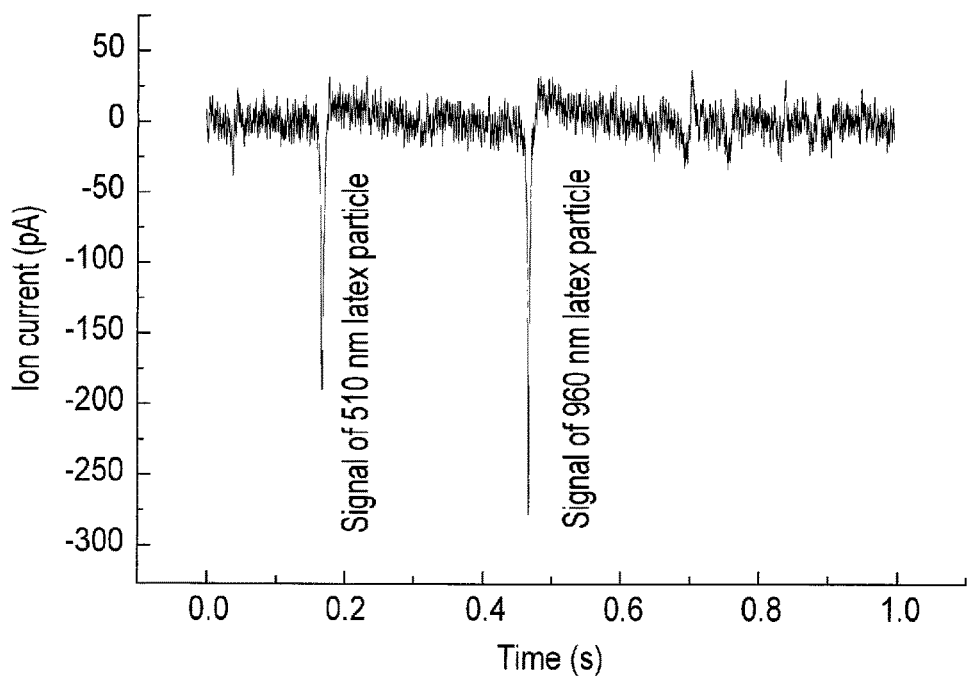
FIG. 6 shows a time response-current change relationship obtained by the measurement device of example 5.

Then, target particles 9 were dispersed in the first electrolytic solution 10 (phosphate buffer solution) in the first chamber 4. The target particles 9 were a mixture of polystyrene latex particles having a 510 nm diameter and polystyrene latex particles having a 960 nm diameter, and were dispersed in the solution 10 in the same concentration as in example 1. Then, the treatment as in example 1 was performed and a time response-current change relationship indicative of a change in current (ion current) with respect to a recorded time (1.0 seconds) was measured as in FIG. 6. In FIG. 6, the base current value having a characteristic value was shifted to 0 pA as an absolute value of the current.

As is evident from FIG. 6, a base line of noise of the current progresses within an amplitude of approximately 50 pA (P-P). When a latex particle of 510 nm diameter passes through the through hole of 2 µm diameter, a drop of approximately 180 pA in the current value was observed, and when a latex particle of 960 nm diameter passes through the through hole, a drop of approximately 275 pA in the current value was observed. Therefore, as explained in the section of example 1, there is evidently a correlation between the size of latex particle and the degree of drop of current value.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 6 is compared to the reference data, and the particle size of each latex particle (target particle) can be acquired.

Example 6

A measurement device having the structure shown in FIG. 1 was prepared as in example 1 except that a first electrode 12 is made of Au and a second electrode 13 is made of Cu which has a greater ionization tendency as compared to Au of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.766 V.

Then, target particles 9 were dispersed in the first electrolytic solution 10 (phosphate buffer solution) in the first chamber 4. The target particles 9 were a mixture of polystyrene latex particles having a 510 nm diameter and polystyrene latex particles having a 960 nm diameter, and were dispersed in the solution 10 in the same concentration as in example 1. Then, the treatment as in example 1 was performed and a time response-current change relationship indicative of a change in current (ion current) with respect to a recorded time (1.0 seconds) was measured as in FIG. 7.

Figure 7:
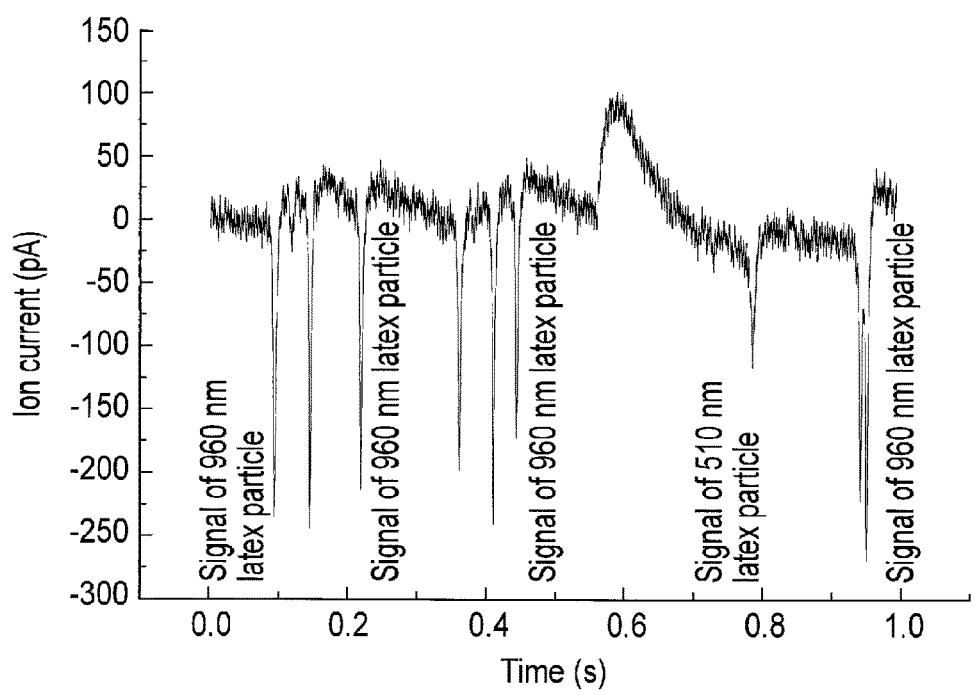
FIG. 7 shows a time response-current change relationship obtained by the measurement device of example 6.

In FIG. 7, the base current value having a characteristic value was shifted to 0 pA as an absolute value of the current.

As is evident from FIG. 7, a base line of noise of the current progresses within an amplitude of approximately 40 pA (P-P). When a latex particle of 510 nm diameter passes through the through hole of 2 µm diameter, a drop of approximately 100 pA in the current value was observed, and when a latex particle of 960 nm diameter passes through the through hole, eight drops including prominent three drops of approximately 245, 240, and 270 pA in the current value were observed within 1.0 seconds. Therefore, as explained in the section of example 1, there is evidently a correlation between the size of latex particle and the degree of drop of current value.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 7 is compared to the reference data, and the particle size of each latex particle (target particle) can be acquired.

Example 7

A measurement device having the structure shown in FIG. 1 was prepared as in example 1 except that a first electrode 12 is made of Pt and a second electrode 13 is made of Cu which has a greater ionization tendency as compared to Pt of the first electrode 12. Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.714 V.

Then, target particles 9 were dispersed in the first electrolytic solution 10 (phosphate buffer solution) in the first chamber 4. The target particles 9 were a mixture of polystyrene latex particles having a 510 nm diameter and polystyrene latex particles having a 960 nm diameter, and were dispersed in the solution 10 in the same concentration as in example 1. Then, the treatment as in example 1 was performed and a time response-current change relationship indicative of a change in current (ion current) with respect to a recorded time (1.0 seconds) was measured as in FIG. 8 In FIG. 8, the base current value having a characteristic value was shifted to 0 pA as an absolute value of the current.

Figure 8:
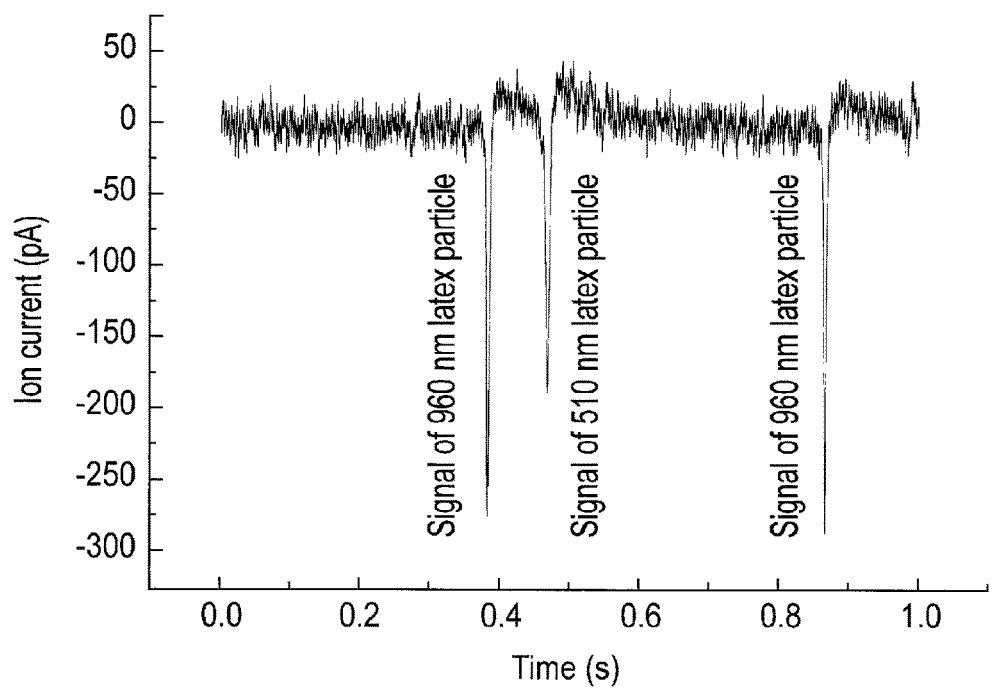
FIG. 8 shows a time response-current change relationship obtained by the measurement device of example 7.

As is evident from FIG. 8, a base line of noise of the current progresses within an amplitude of approximately 50 pA (P-P). When a latex particle of 510 nm diameter passes through the through hole of 2 µm diameter, a drop of approximately 175 pA in the current value was observed, and when a latex particle of 960 nm diameter passes through the through hole, two drops of approximately 270 and 280 pA in the current value were observed within 1.0 seconds. Therefore, as explained in the section of example 1, there is evidently a correlation between the size of latex particle and the degree of drop of current value.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 8 is compared to the reference data, and the particle size of each latex particle (target particle) can be acquired.

Example 8

A measurement device having the structure shown in FIG. 1 was prepared as in example 1 except that a first electrode 12 is made of Ag and a second electrode 13 is made of Cu which has a greater ionization tendency as compared to Ag of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.682 V.

Figure 9:
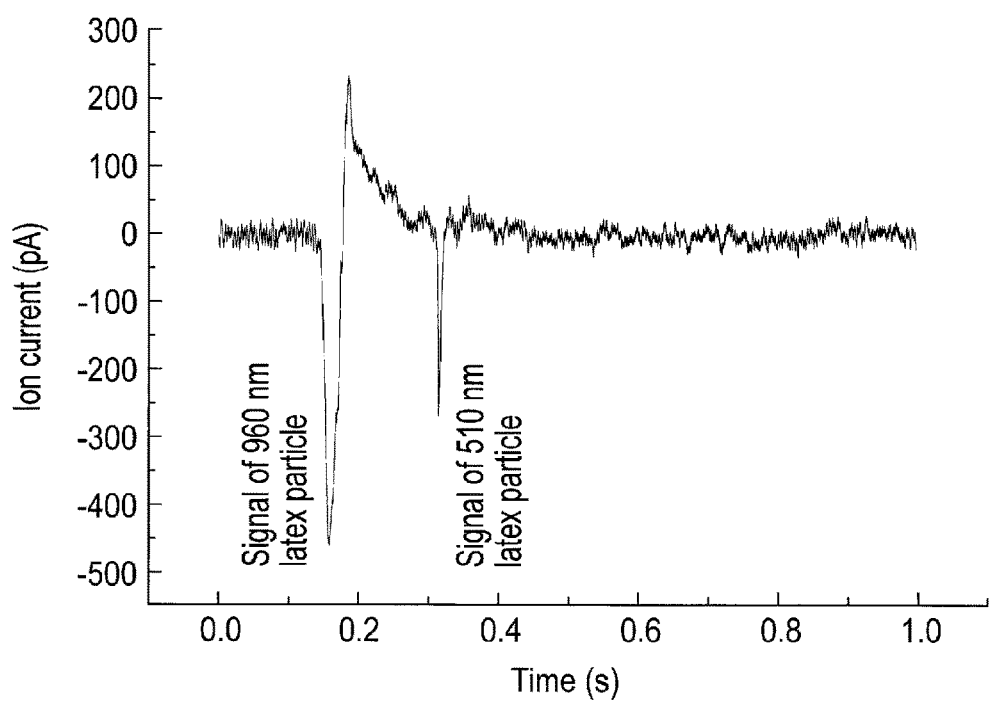
FIG. 9 shows a time response-current change relationship obtained by the measurement device of example 8.

Then, target particles 9 were dispersed in the first electrolytic solution 10 (phosphate buffer solution) in the first chamber 4. The target particles 9 were a mixture of polystyrene latex particles having a 510 nm diameter and polystyrene latex particles having a 960 nm diameter, and were dispersed in the solution 10 in the same concentration as in example 1. Then, the treatment as in example 1 was performed and a time response-current change relationship indicative of a change in current (ion current) with respect to a recorded time (1.0 seconds) was measured as in FIG. 9. In FIG. 9, the base current value having a characteristic value was shifted to 0 pA as an absolute value of the current.

As is evident from FIG. 9, a base line of noise of the current progresses within an amplitude of approximately 30 pA (P-P). When a latex particle of 510 nm diameter passes through the through hole of 2 μm diameter, a drop of approximately 250 pA in the current value was observed, and when a latex particle of 960 nm diameter passes through the through hole, a drop of approximately 450 pA in the current value was observed. Therefore, as explained in the section of example 1, there is evidently a correlation between the size of latex particle and the degree of drop of current value.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 9 is compared to the reference data, and the particle size of each latex particle (target particle) can be acquired.

Example 9

A measurement device having the structure shown in FIG. 1 was prepared as in example 1 except that a first electrode 12 is made of Au and a second electrode 13 is made of Ni which has a greater ionization tendency as compared to Au of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.644 V.

Then, target particles 9 were dispersed in the first electrolytic solution 10 (phosphate buffer solution) in the first chamber 4. The target particles 9 were a mixture of polystyrene latex particles having a 510 nm diameter and polystyrene latex particles having a 960 nm diameter, and were dispersed in the solution 10 in the same concentration as in example 1. Then, the treatment as in example 1 was performed and a time response-current change relationship indicative of a change in current (ion current) with respect to a recorded time (1.0 seconds) was measured as in FIG. 10. In FIG. 10, the base current value having a characteristic value was shifted to 0 pA as an absolute value of the current.

As is evident from FIG. 10, a base line of noise of the current progresses within an amplitude of approximately 50 pA (P-P). When a latex particle of 510 nm diameter passes through the through hole of 2 μm diameter, a drop of approximately 175 pA in the current value was observed, and when a latex particle of 960 nm diameter passes through the through hole, a drop of approximately 275 pA in the current value was observed. Therefore, as explained in the section of example 1, there is evidently a correlation between the size of latex particle and the degree of drop of current value.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 10 is compared to the reference data, and the particle size of each latex particle (target particle) can be acquired.

Example 10

A measurement device having the structure shown in FIG. 1 was prepared as in example 1 except that a first electrode 12 is made of Pt and a second electrode 13 is made of Ni which has a greater ionization tendency as compared to Pt of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.628 V.

Then, target particles 9 were dispersed in the first electrolytic solution 10 (phosphate buffer solution) in the first chamber 4. The target particles 9 were a mixture of polystyrene latex particles having a 510 nm diameter and polystyrene latex particles having a 960 nm diameter, and were dispersed in the solution 10 in the same concentration as in example 1. Then, the treatment as in example 1 was performed and a time response-current change relationship indicative of a change in current (ion current) with respect to a recorded time (1.0 seconds) was measured as in FIG. 11. In FIG. 11, the base current value having a characteristic value was shifted to 0 pA as an absolute value of the current.

As is evident from FIG. 11, a base line of noise of the current progresses within an amplitude of approximately 40 pA (P-P). When a latex particle of 510 nm diameter passes through the through hole of 2 μm diameter, three drops of approximately 220, 270, and 210 pA in the current value were observed within 1.0 seconds, and when a latex particle of 960 nm diameter passes through the through hole, a drop of approximately 450 pA in the current value was observed. Therefore, as explained in the section of example 1, there is evidently a correlation between the size of latex particle and the degree of drop of current value.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 11 is compared to the reference data, and the particle size of each latex particle (target particle) can be acquired.

Example 11

A measurement device having the structure shown in FIG. 1 was prepared as in example 1 except that a first electrode 12 is made of Ag and a second electrode 13 is made of Ni which has a greater ionization tendency as compared to Ag of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.593 V.

Then, target particles 9 were dispersed in the first electrolytic solution 10 (phosphate buffer solution) in the first chamber 4. The target particles 9 were a mixture of polystyrene latex particles having a 510 nm diameter and polystyrene latex particles having a 960 nm diameter, and were dispersed in the solution 10 in the same concentration as in example 1. Then, the treatment as in example 1 was performed and a time response-current change relationship indicative of a change in current (ion current) with respect to a recorded time (1.0 seconds) was measured as in FIG. 12. In FIG. 12, the base current value having a characteristic value was shifted to 0 pA as an absolute value of the current.

As is evident from FIG. 12, a base line of noise of the current progresses within an amplitude of approximately 50 pA (P-P). When a latex particle of 510 nm diameter passes through the through hole of 2 µm diameter, a drop of approximately 175 pA in the current value was observed, and when a latex particle of 960 nm diameter passes through the through hole, four drops of approximately 260, 295, 275, and 225 pA in the current value were observed within 1.0 seconds. Therefore, as explained in the section of example 1, there is evidently a correlation between the size of latex particle and the degree of drop of current value.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 12 is compared to the reference data, and the particle size of each latex particle (target particle) can be acquired.

Example 12

A measurement device having the structure shown in FIG. 1 was prepared as in example 1 except that a first electrode 12 is made of Au and a second electrode 13 is made of Co which has a greater ionization tendency as compared to Au of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.6 V.

Then, target particles 9 were dispersed in the first electrolytic solution 10 (phosphate buffer solution) in the first chamber 4. The target particles 9 were a mixture of polystyrene latex particles having a 510 nm diameter and polystyrene latex particles having a 960 nm diameter, and were dispersed in the solution 10 in the same concentration as in example 1. Then, the treatment as in example 1 was performed and a time response-current change relationship indicative of a change in current (ion current) with respect to a recorded time (1.0 seconds) was measured as in FIG. 13. In FIG. 13, the base current value having a characteristic value was shifted to 0 pA as an absolute value of the current.

As is evident from FIG. 13, a base line of noise of the current progresses within an amplitude of approximately 40 pA (P-P). When a latex particle of 510 nm diameter passes through the through hole of 2 µm diameter, a drop of approximately 180 pA in the current value was observed, and when a latex particle of 960 nm diameter passes through the through hole, two drops of approximately 260 and 270 pA in the current value were observed within 1.0 seconds. Therefore, as explained in the section of example 1, there is evidently a correlation between the size of latex particle and the degree of drop of current value.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 13 is compared to the reference data, and the particle size of each latex particle (target particle) can be acquired.

Example 13

A measurement device having the structure shown in FIG. 1 was prepared as in example 1 except that a first electrode 12 is made of Pt and a second electrode 13 is made of Co which has a greater ionization tendency as compared to Pt of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.622 V.

Then, target particles 9 were dispersed in the first electrolytic solution 10 (phosphate buffer solution) in the first chamber 4. The target particles 9 were a mixture of polystyrene latex particles having a 510 nm diameter and polystyrene latex particles having a 960 nm diameter, and were dispersed in the solution 10 in the same concentration as in example 1. Then, the treatment as in example 1 was performed and a time response-current change relationship indicative of a change in current (ion current) with respect to a recorded time (1.0 seconds) was measured as in FIG. 14. In FIG. 14, the base current value having a characteristic value was shifted to 0 pA as an absolute value of the current.

As is evident from FIG. 14, a base line of noise of the current progresses within an amplitude of approximately 50 pA (P-P). When a latex particle of 510 nm diameter passes through the through hole of 2 μm diameter, a drop of approximately 170 pA in the current value was observed, and when a latex particle of 960 nm diameter passes through the through hole, three drops of approximately 270, 225, and 235 pA in the current value were observed within 1.0 seconds. Therefore, as explained in the section of example 1, there is evidently a correlation between the size of latex particle and the degree of drop of current value.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 14 is compared to the reference data, and the particle size of each latex particle (target particle) can be acquired.

Example 14

A measurement device having the structure shown in FIG. 1 was prepared as in example 1 except that a first electrode 12 is made of Au and a second electrode 13 is made of W which has a greater ionization tendency as compared to Au of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.68 V.

Then, target particles 9 were dispersed in the first electrolytic solution 10 (TE buffer solution) in the first chamber 4. The target particles 9 were polystyrene latex particles having a 960 nm diameter dispersed in a concentration of $1\times10^7$ particles/mL. Then, the treatment as in example 1 was performed and a time response-current change relationship indicative of a change in current (ion current) with respect to a recorded time (1.0 seconds) was measured as in FIG. 15. In FIG. 15, the base current value having a characteristic value was shifted to 0 pA as an absolute value of the current.

As is evident from FIG. 15, a base line of noise of the current progresses within an amplitude of approximately 40 pA (P-P). When a latex particle of 960 nm diameter passes through the through hole of 2 μm diameter, two drops of approximately 285 and 270 pA in the current value were observed within 1.0 seconds.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 15 is compared to the reference data, and the particle size of each latex particle (target particle) can be acquired.

Example 15

A measurement device having the structure shown in FIG. 1 was prepared as in example 1 except that a first electrode 12 is made of Ag and a second electrode 13 is made of W which has a greater ionization tendency as compared to Ag of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.678 V.

Figure 16:
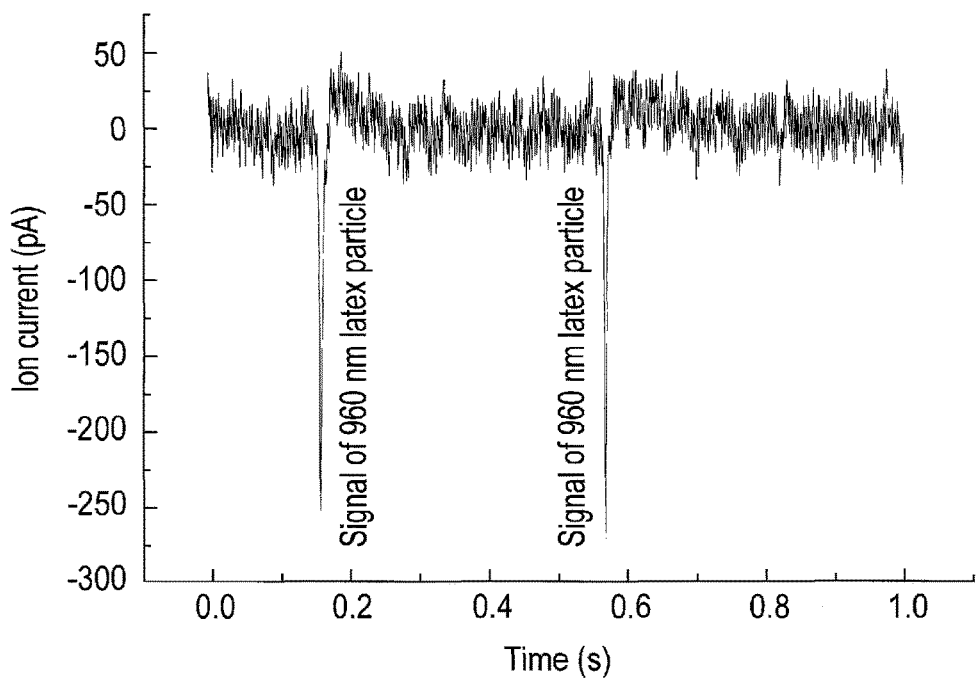
FIG. 16 shows a time response-current change relationship obtained by the measurement device of example 15.

Then, target particles 9 were dispersed in the first electrolytic solution 10 (phosphate buffer solution) in the first chamber 4. The target particles 9 were polystyrene latex particles having a 960 nm diameter, and were dispersed in the solution 10 in the same concentration as in example 14. Then, the treatment as in example 1 was performed and a time response-current change relationship indicative of a change in current (ion current) with respect to a recorded time (1.0 seconds) was measured as in FIG. 16. In FIG. 16, the base current value having a characteristic value was shifted to 0 pA as an absolute value of the current.

As is evident from FIG. 16, a base line of noise of the current progresses within an amplitude of approximately 50 pA (P-P). When a latex particle of 960 nm diameter passes through the through hole of 2 μm diameter, two drops of approximately 255 and 275 pA in the current value were observed within 1.0 seconds.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 16 is compared to the reference data, and the particle size of each latex particle (target particle) can be acquired.

Example 16

A measurement device having the structure shown in FIG. 1 was prepared as in example 1 except that a first electrode 12 is made of Pt and a second electrode 13 is made of W which has a greater ionization tendency as compared to Pt of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.58 V.

Figure 17:
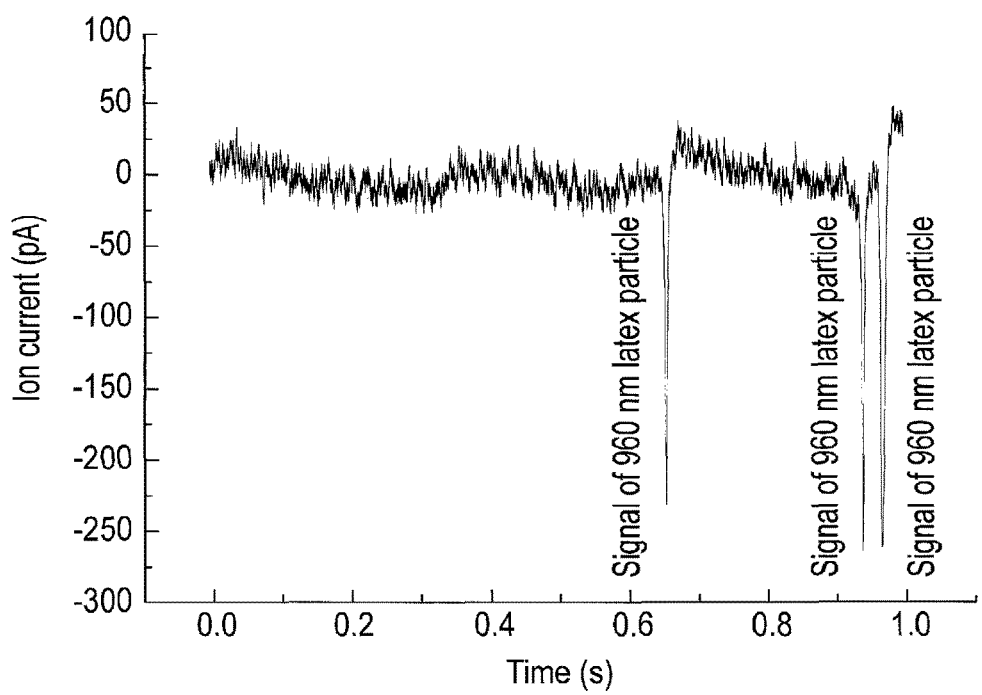
FIG. 17 shows a time response-current change relationship obtained by the measurement device of example 16.

Then, target particles 9 were dispersed in the first electrolytic solution 10 (phosphate buffer solution) in the first chamber 4. The target particles 9 were polystyrene latex particles having a 960 nm diameter, and were dispersed in the solution 10 in the same concentration as in example 14. Then, the treatment as in example 1 was performed and a time response-current change relationship indicative of a change in current (ion current) with respect to a recorded time (1.0 seconds) was measured as in FIG. 17. In FIG. 17, the base current value having a characteristic value was shifted to 0 pA as an absolute value of the current.

As is evident from FIG. 17, a base line of noise of the current progresses within an amplitude of approximately 40 pA (P-P). When a latex particle of 960 nm diameter passes through the through hole of 2 μm diameter, three drops of approximately 240, 270, and 265 pA in the current value were observed within 1.0 seconds.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 17 is compared to the reference data, and the particle size of each latex particle (target particle) can be acquired.

Example 17

A measurement device having the structure shown in FIG. 1 was prepared as in example 1 except that a first electrode 12 is made of Cu and a second electrode 13 is made of W which has a greater ionization tendency as compared to Cu of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.603 V.

Figure 18:
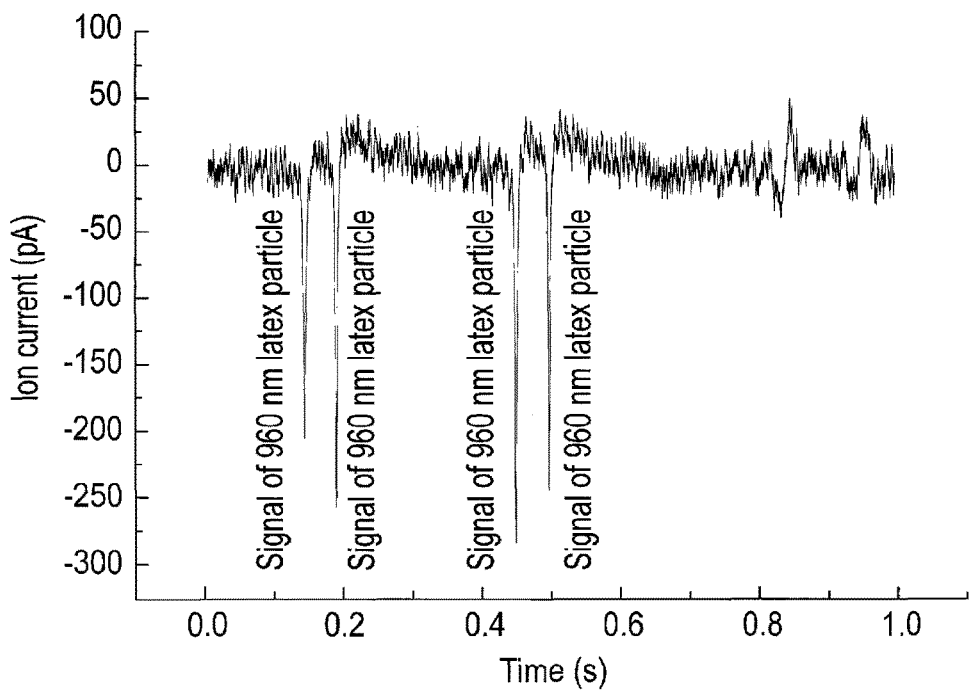
FIG. 18 shows a time response-current change relationship obtained by the measurement device of example 17.

Then, target particles 9 were dispersed in the first electrolytic solution 10 (phosphate buffer solution) in the first chamber 4. The target particles 9 were polystyrene latex particles having a 960 nm diameter, and were dispersed in the solution 10 in the same concentration as in example 14. Then, the treatment as in example 1 was performed and a time response-current change relationship indicative of a change in current (ion current) with respect to a recorded time (1.0 seconds) was measured as in FIG. 18. In FIG. 18, the base current value having a characteristic value was shifted to 0 pA as an absolute value of the current.

As is evident from FIG. 18, a base line of noise of the current progresses within an amplitude of approximately 40 pA (P-P). When a latex particle of 960 nm diameter passes through the through a hole of 2 μm diameter, four drops of approximately 200, 255, 280, and 240 pA in the current value were observed within 1.0 seconds.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 18 is compared to the reference data, and the particle size of each latex particle (target particle) can be acquired.

Example 18

A measurement device having the structure shown in FIG. 1 was prepared as in example 1 except that a first electrode 12 is made of Au and a second electrode 13 is made of Ti which has a greater ionization tendency as compared to Au of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.599 V.

Figure 19:
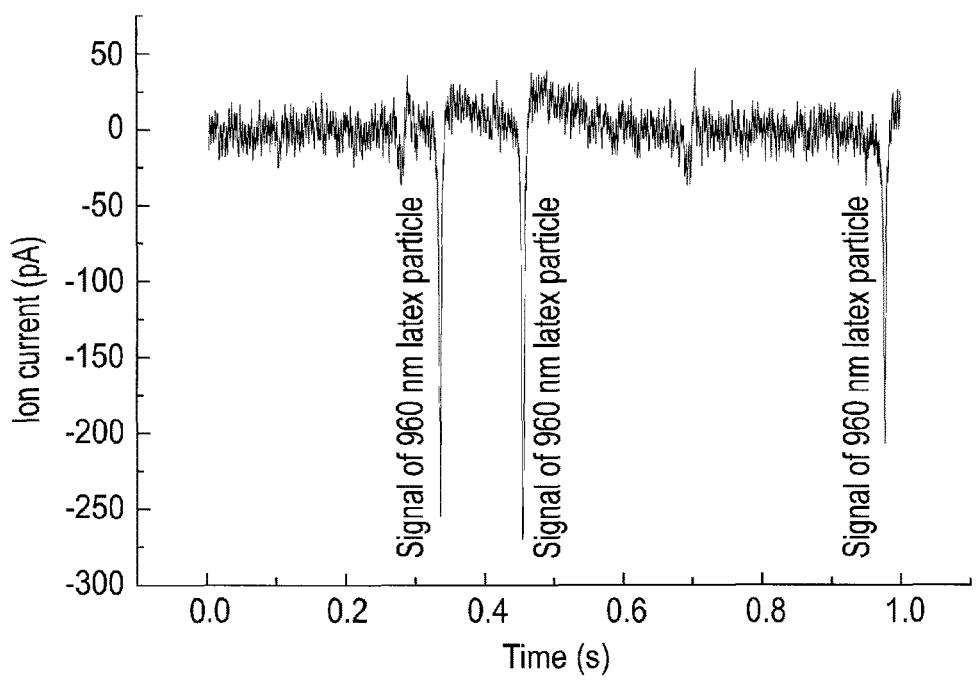
FIG. 19 shows a time response-current change relationship obtained by the measurement device of example 18.

Then, target particles 9 were dispersed in the first electrolytic solution 10 (phosphate buffer solution) in the first chamber 4. The target particles 9 were polystyrene latex particles having a 960 nm diameter, and were dispersed in the solution 10 in the same concentration as in example 14. Then, the treatment as in example 1 was performed and a time response-current change relationship indicative of a change in current (ion current) with respect to a recorded time (1.0 seconds) was measured as in FIG. 19. In FIG. 19, the base current value having a characteristic value was shifted to 0 pA as an absolute value of the current.

As is evident from FIG. 19, a base line of noise of the current progresses within an amplitude of approximately 40 pA (P-P). When a latex particle of 960 nm diameter passes through the through hole of 2 μm diameter, three drops of approximately 260, 275, and 210 pA in the current value were observed within 1.0 seconds.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 19 is compared to the reference data, and the particle size of each latex particle (target particle) can be acquired.

Example 19

A measurement device having the structure shown in FIG. 1 was prepared as in example 1 except that a first electrode 12 is made of Pt and a second electrode 13 is made of Ti which has a greater ionization tendency as compared to Pt of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.611 V.

Figure 20:
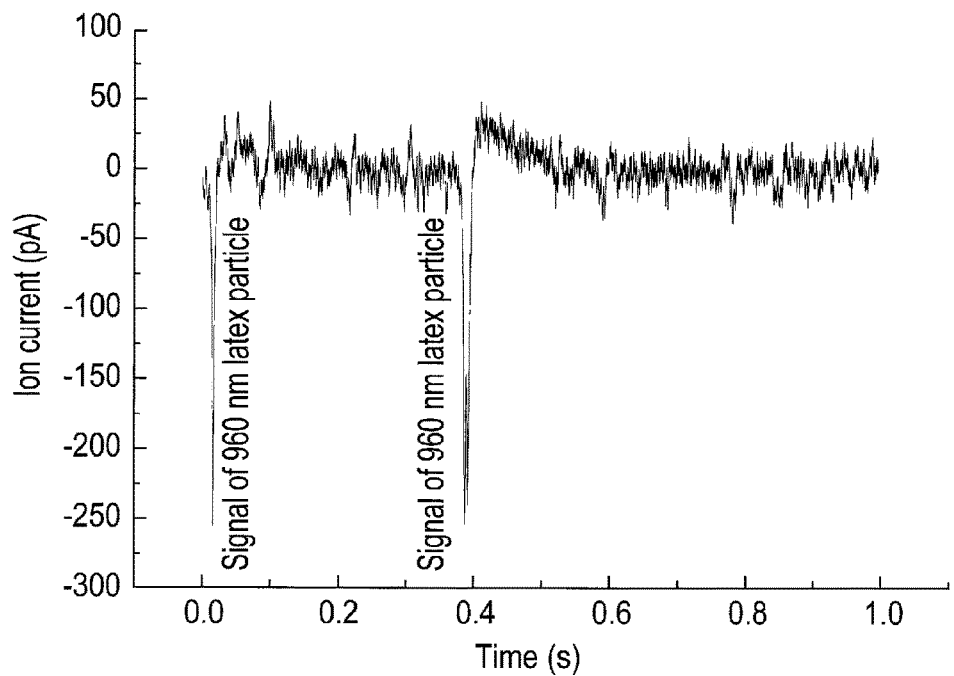
FIG. 20 shows a time response-current change relationship obtained by the measurement device of example 19.

Then, target particles 9 were dispersed in the first electrolytic solution 10 (phosphate buffer solution) in the first chamber 4. The target particles 9 were polystyrene latex particles having a 960 nm diameter, and were dispersed in the solution 10 in the same concentration as in example 14. Then, the treatment as in example 1 was performed and a time response-current change relationship indicative of a change in current (ion current) with respect to a recorded time (1.0 seconds) was measured as in FIG. 20. In FIG. 20, the base current value having a characteristic value was shifted to 0 pA as an absolute value of the current.

As is evident from FIG. 20, a base line of noise of the current progresses within an amplitude of approximately 50 pA (P-P). When a latex particle of 960 nm diameter passes through the through hole of 2 μm diameter, two drops of both approximately 260 pA in the current value were observed within 1.0 seconds.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 20 is compared to the reference data, and the particle size of each latex particle (target particle) can be acquired.

Example 20

A measurement device having the structure shown in FIG. 1 was prepared as in example 1 except that a first electrode 12 is made of Ag and a second electrode 13 is made of Ti which has a greater ionization tendency as compared to Ag of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.617 V.

Figure 21:
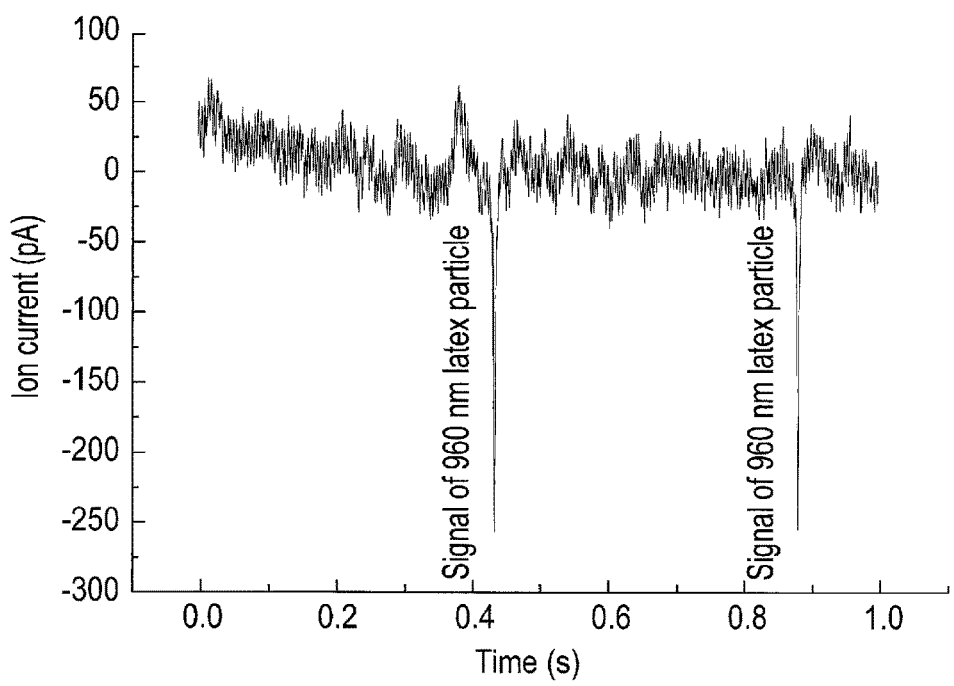
FIG. 21 shows a time response-current change relationship obtained by the measurement device of example 20.

Then, target particles 9 were dispersed in the first electrolytic solution 10 (phosphate buffer solution) in the first chamber 4. The target particles 9 were polystyrene latex particles having a 960 nm diameter, and were dispersed in the solution 10 in the same concentration as in example 14. Then, the treatment as in example 1 was performed and a time response-current change relationship indicative of a change in current (ion current) with respect to a recorded time (1.0 seconds) was measured as in FIG. 21. In FIG. 21, the base current value having a characteristic value was shifted to 0 pA as an absolute value of the current.

As is evident from FIG. 21, a base line of noise of the current progresses within an amplitude of approximately 40 pA (P-P). When a latex particle of 960 nm diameter passes through the through hole of 2 μm diameter, two drops of approximately 260 and 255 pA in the current value were observed within 1.0 seconds.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 21 is compared to the reference data, and the particle size of each latex particle (target particle) can be acquired.

Example 21

A measurement device having the structure shown in FIG. 1 was prepared as in example 1 except that a first electrode 12 is made of Cu and a second electrode 13 is made of Ti which has a greater ionization tendency as compared to Cu of the first electrode 12.

Initially, electrolytic solutions 10 and 11 (phosphate buffer solution at room temperature) prepared as in example 2 were filled in the first and second chambers 4 and 5, and in this state, a voltage between the first electrode 12 and the second electrode 13 was measured as in example 1. As a result, a potential difference between the first and second electrodes 12 and 13 was approximately 0.572 V.

Then, target particles 9 were dispersed in the first electrolytic solution 10 (phosphate buffer solution) in the first chamber 4. The target particles 9 were polystyrene latex particles having a 960 nm diameter, and were dispersed in the solution 10 in the same concentration as in example 14. Then, the treatment as in example 1 was performed and a time response-current change relationship indicative of a change in current (ion current) with respect to a recorded time (1.0 seconds) was measured as in FIG. 22. In FIG. 22, the base current value having a characteristic value was shifted to 0 pA as an absolute value of the current.

As is evident from FIG. 22, a base line of noise of the current progresses within an amplitude of approximately 40 pA (P-P). When a latex particle of 960 nm diameter passes through the through hole of 2 μm diameter, two drops of approximately 295 and 275 pA in the current value were observed within 1.0 seconds.

In the actual particle size measurement process, several kinds of publically-known latex particles having different particles sizes are measured by a measurement device including the sensor 1 and the current voltage converter circuit 21 structured as in this example, and reference data of the time response-current change relationship of the particles are prepared. The time response-current change relationship shown in FIG. 22 is compared to the reference data, and the particle size of each latex particle (target particle) can be acquired.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A measurement device comprising:
a first chamber;
a second chamber;
a partition provided between the first chamber and the second chamber;
a through hole which is provided in the partition and with which the first chamber and the second chamber communicate each other;
a first electrode provided in the first chamber; and
a second electrode provided in the second chamber, wherein
the first electrode and the second electrode contain different metals or alloys at least in surface layers thereof, and a relationship of Ia<Ib is satisfied, where Ia is an ionization tendency of a metal or an alloy contained at least in the surface layer of the first electrode and Ib is an ionization tendency of a metal or an alloy contained at least in the surface layer of the second electrode.

2. The device of claim 1, wherein the through hole has a diameter which is greater than that of a target particle.

3. The device of claim 2, wherein the target particle is at least one selected from a bacterium, virus, protein, and DNA.

4. The device of claim 1, wherein a battery reaction is generated between the first electrode and the second electrode.

5. The device of claim 4, wherein an electromotive force of the battery reaction is 200 nA or less.

6. The device of claim 1, wherein the second electrode is an electrode at least of which surface layer is made of Ag/AgCl, or of at least one metal selected from a group consisting of Al, Cu, Ni, Co, W, and Ti, or of an alloy selected from the same, and the first electrode is an electrode at least of which surface layer is made of at least one metal selected from a group consisting of Au, Pt, Ag, Cu, Ni, Co, Ti, and Al, or of an alloy selected from the same where the ionization tendency of the latter group is less than that of the former group.

7. The device of claim 1, wherein combinations of the metal or the alloy contained at least in the surface layer of the first and second electrodes satisfying the relationship $Ia<Ib$ are (1) first electrode: Al and second electrode: Ag/AgCl (AgCl formed as a coating of Ag), (2) first electrode: Au and second electrode: Al, (3) first electrode: Pt and second electrode: Al, (4) first electrode: Cu and second electrode: Al, (5) first electrode: Ti and second electrode: Al, (6) first electrode: Au and second electrode: Cu, (7) first electrode: Pt and second electrode: Cu, (8) first electrode: Ag and second electrode: Cu, (9) first electrode: Au and second electrode: Ni, (10) first electrode: Pt and second electrode: Ni, (11) first electrode: Ag and second electrode: Ni, (12) first electrode: Au and second electrode: Co, (13) first electrode: Au and second electrode: W, (14) first electrode: Pt and second electrode: W, (15) first electrode: Cu and second electrode: W, (16) first electrode: Au and second electrode: Ti, (17) first electrode: Pt and second electrode: Ti, (18) first electrode: Cu and second electrode: Ti, where a potential difference between the first and second electrodes produces an electromotive force of approximately 0.05 V or more.

8. The device of claim 1, wherein the first electrode is made of a metal or an alloy, and the second electrode is made of a metal or an alloy which is different from that of the first electrode.

9. The device of claim 1, wherein the first electrode is made of a metal or an alloy, and the second electrode comprises a second electrode main body and a second surface layer provided on the second electrode main body, the second surface layer made of a metal or an alloy which is different from that of the first electrode.

10. The device of claim 1, wherein the first electrode comprises a first electrode main body and a first surface layer provided on the first electrode main body, the first surface layer being made of a metal or an alloy, and the second electrode is made of a metal or an alloy which is different from that of the first surface layer of the first electrode.

11. The device of claim 1, wherein the first electrode comprises a first electrode main body and a first surface layer provided on the first electrode main body, the first surface layer being made of a metal or an alloy, and the second electrode comprises a second electrode main body and a second surface layer provided on the second electrode main body, the second surface layer being made of a metal or an alloy which is different from that of the first surface layer of the first electrode.

12. The device of claim 1, wherein the first chamber is positioned above the second chamber.

13. The device of claim 1, further comprising a current voltage converter circuit connected to the first and second electrodes.

14. The device of claim 13, wherein the current voltage converter circuit comprises a current voltage converter amplifier including input terminals to which the first and second electrodes are connected, and a current voltage converter resistance connected between an output terminal and one of the input terminals of the current voltage converter amplifier.

* * * * *